United States Patent
Tank

(10) Patent No.: US 9,283,061 B2
(45) Date of Patent: Mar. 15, 2016

(54) METHOD AND ANALYSIS SYSTEM FOR THE GEOMETRICAL ANALYSIS OF SCAN DATA FROM ORAL STRUCTURES

(75) Inventor: Martin Tank, Heidelberg (DE)

(73) Assignee: STRAUMANN HOLDING AG, Basel (CH)

(*) Notice: Subject to any disclaimer, the term of this patent is extended or adjusted under 35 U.S.C. 154(b) by 0 days.

(21) Appl. No.: 13/983,753

(22) PCT Filed: Dec. 12, 2011

(86) PCT No.: PCT/EP2011/006256
§ 371 (c)(1),
(2), (4) Date: Aug. 5, 2013

(87) PCT Pub. No.: WO2012/107069
PCT Pub. Date: Aug. 16, 2012

(65) Prior Publication Data
US 2013/0308843 A1   Nov. 21, 2013

(30) Foreign Application Priority Data
Feb. 10, 2011 (DE) .......................... 10 2011 010 975

(51) Int. Cl.
| G06K 9/00 | (2006.01) |
| A61C 19/04 | (2006.01) |
| G06T 7/00 | (2006.01) |
| A61C 9/00 | (2006.01) |
| A61B 6/00 | (2006.01) |

(52) U.S. Cl.
CPC ............... *A61C 19/04* (2013.01); *A61C 9/0053* (2013.01); *G06T 7/0083* (2013.01); *G06T 7/0089* (2013.01); *A61B 6/506* (2013.01); *G06T 2207/30036* (2013.01)

(58) Field of Classification Search
None
See application file for complete search history.

(56) References Cited

U.S. PATENT DOCUMENTS

| 7,040,896 B2 | 5/2006 | Pavlovskaia et al. | |
| 7,373,286 B2 * | 5/2008 | Nikolskiy et al. | 703/7 |
| 7,476,100 B2 * | 1/2009 | Kuo | 433/6 |

(Continued)

FOREIGN PATENT DOCUMENTS

| DE | 1964227 C1 | 1/1998 |
| DE | 10357206 A1 | 7/2005 |

(Continued)

OTHER PUBLICATIONS

International Search Report; PCT/EP2011/006256; Mar. 28, 2012.
(Continued)

*Primary Examiner* — Nancy Bitar
(74) *Attorney, Agent, or Firm* — Studebaker & Brackett PC

(57) ABSTRACT

The invention describes a method for the geometrical analysis of scan data from oral structures, comprising the steps of selecting a number of parameterized tooth models of desired tooth types according to the scan data to be analyzed, whereby each tooth model comprises at least one boundary line whose path is defined by line parameters and which divides a tooth model in at least one active adjustment area and at least one inactive adjustment area, and segmenting the scan data on the basis of individualized tooth models and individualized boundary lines and/or determining at least one boundary line in the scan data. The invention further describes a method of generating a model database; and an analysis system for the geometrical analysis of scan data from oral structures.

16 Claims, 9 Drawing Sheets

(56) References Cited

U.S. PATENT DOCUMENTS

| | | | |
|---|---|---|---|
| 7,496,217 B2 | 2/2009 | Tank | |
| 7,583,272 B2 * | 9/2009 | Ramani | G06F 17/30277 345/621 |
| 7,865,261 B2 | 1/2011 | Pfeiffer | |
| 8,026,943 B2 * | 9/2011 | Weber et al. | 348/77 |
| 8,274,508 B2 * | 9/2012 | Porikli | G06K 9/6214 345/419 |
| 8,727,776 B2 * | 5/2014 | Mehl | 433/223 |
| 8,994,723 B2 * | 3/2015 | Drost | G06K 9/00201 345/419 |
| 2004/0044787 A1 * | 3/2004 | Vipat | 709/238 |
| 2005/0123197 A1 | 6/2005 | Tank | |
| 2006/0063135 A1 | 3/2006 | Mehl | |
| 2006/0111631 A1 * | 5/2006 | Kelliher et al. | 600/425 |
| 2008/0020350 A1 * | 1/2008 | Matov et al. | 433/213 |
| 2008/0310757 A1 * | 12/2008 | Wolberg | G06K 9/00208 382/285 |
| 2009/0081616 A1 * | 3/2009 | Pfeiffer | 433/215 |
| 2010/0004698 A1 * | 1/2010 | De Moyer | 606/86 R |
| 2010/0167243 A1 * | 7/2010 | Spiridonov et al. | 433/224 |
| 2011/0151400 A1 * | 6/2011 | Boiangiu et al. | 433/76 |
| 2011/0213598 A1 * | 9/2011 | Matov et al. | 703/7 |
| 2013/0322719 A1 * | 12/2013 | Dekel | A61B 6/12 382/131 |

FOREIGN PATENT DOCUMENTS

| | | |
|---|---|---|
| DE | 102005033738 A1 | 1/2007 |
| DE | 102007033998 A1 | 4/2008 |
| GB | 2440267 A | 1/2008 |
| WO | 2004/044787 A2 | 5/2004 |

OTHER PUBLICATIONS

V. Blanz V et al.: "A statistical method for robust 3D surface reconstruction from sparse data"; 3D Data Processing, Visualization and Transmission, 2004. 3DPVT 2004.; Proceedings. 2nd International Symposium on Thessaloniki; Greece Sep. 6-9, 2004, Piscataway, NJ, USA, IEEE, Seiten 293-300, XP010725119, DOI: 10.1109/TDPVT. 2004.1335212 ISBN: 978-0-7695-2223-4 Summary Chapter I. Introduction Kapitel X. A biogeneric Mor-phable Model of Teeth.

U.S. Appl. No. 13/978,106, filed Jul. 2, 2013.

\* cited by examiner

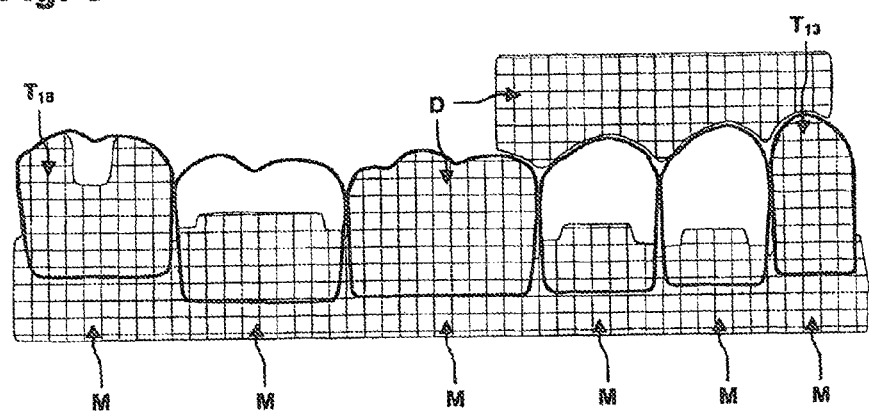
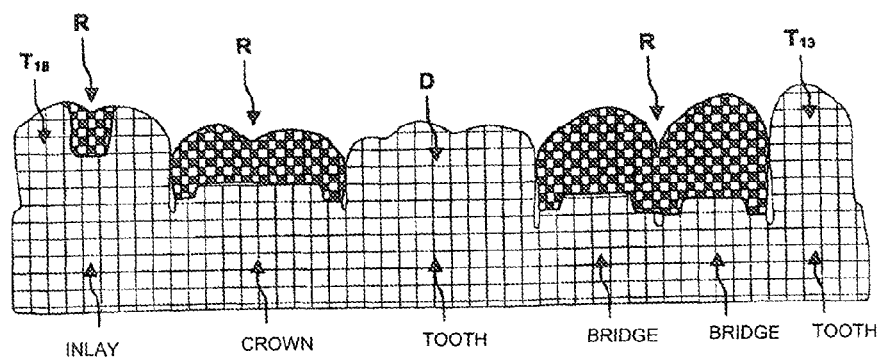

| 18 | 17 | 16 | 15 | 14 | 13 | 12 | 11 | 21 | 22 | 23 | 24 | 25 | 26 | 27 | 28 |
|---|---|---|---|---|---|---|---|---|---|---|---|---|---|---|---|
| x | x | x | x | x | x | - | - | - | - | - | - | - | - | - | - |
| 48 | 47 | 46 | 45 | 44 | 43 | 42 | 41 | 31 | 32 | 33 | 34 | 35 | 36 | 37 | 38 |
| - | - | - | - | - | - | - | - | - | - | - | - | - | - | - | - |

| 18 | 17 | 16 | 15 | 14 | 13 | 12 | 11 | 21 | 22 | 23 | 24 | 25 | 26 | 27 | 28 |
|---|---|---|---|---|---|---|---|---|---|---|---|---|---|---|---|
| Inlay | Crown | Tooth | Bridge | Bridge | Tooth | - | - | - | - | - | - | - | - | - | - |
| 48 | 47 | 46 | 45 | 44 | 43 | 42 | 41 | 31 | 32 | 33 | 34 | 35 | 36 | 37 | 38 |
| - | - | - | - | - | - | - | - | - | - | - | - | - | - | - | - |

| 18 | 17 | 16 | 15 | 14 | 13 |
|---|---|---|---|---|---|
| Inlay | Crown | Tooth | Bridge | Bridge | Tooth |

METHOD AND ANALYSIS SYSTEM FOR THE GEOMETRICAL ANALYSIS OF SCAN DATA FROM ORAL STRUCTURES

The invention describes a method for the geometrical analysis of scan data from oral structures, which can be used particularly in the field of digital dental technology. The information determined is of primary importance for the manufacture of dental prostheses or tooth restoration parts using dental CAD/CAM systems. Such systems have become firmly established in dentistry and dental technology, and descriptions of such systems can be found in the exemplary patent documents U.S. Pat. No. 5,217,375A, U.S. Pat. No. 7,708,560 B2, U.S. Pat. No. 7,581,953 B2, EP 06 34 150 A1, EP 09 13 130 A2, DE 10 2005 033 738 A1 and WO 0239056 A1. However, a geometrical analysis of scan data from oral structures is also of primary importance in other fields of digital dental technology. For example, results can be used to good purpose in the field of implantology or orthodontistry, but also for the optimization of measurement procedures of oral structures, by analyzing the scan data during measurement, and using the results to influence the measurement. In the context of the present invention, oral structures are to be understood to mean teeth with neighboring anatomical structures such as gum, jawbone, nerve tracts etc., as well as artificial structures such as implants, abutments, other anchoring systems, brackets, static and dynamic registrations, etc. Furthermore, the invention describes a method for the creation of a model database for use in such a method, as well as an analysis system for the geometrical analysis of scan data from oral structures.

In the field of digital dental technology, scan data of oral structures are generally determined optically or radiologically. Optical scanners for three-dimensional measurement directly from intra-oral surface structures, or from extra-oral impressions of oral surface structures, are widespread and economical. Usually, one obtains triangulated surface data, which can be saved in STL format in the case of open systems. Radiological scanners such as computer tomographs (CT) or digital volume tomographs (DVT) use X-rays to generate volume datasets of oral structures. The medical imaging DICOM format has established itself as a generally accepted data format.

These scan data must, in many cases, be analyzed geometrically during the examination itself or immediately after the examination, in order to optimize the measurement and/or to further plan an examination and/or to make a diagnosis and/or to plan a treatment. The so-called "segmentation" of geometric structures plays a significant role in the analysis of scan data. In such a segmentation, the scan data of the object under examination are fragmented so that certain partial objects of an object under examination, i.e. certain geometric structures that are the focus of that examination, are separated from the rest of the scan data. An example to illustrate this is the separation of teeth from each other and from gum or bone, and the assignment of tooth numbers to the separated teeth. Of course, artificial structures such as implants, brackets etc. can also be separated from the remainder of the scan data during segmentation.

In the field of prosthetics, optical scan data are usually used for the evaluation or computation of virtual tooth restorations on account of the necessary high level of precision. In the context of the present invention, the term "tooth restoration parts" covers every type of producible object for the treatment of dental defects. Examples are inlays, onlays, crowns, telescope crowns, bridges, veneers, implant abutments, partial prostheses and prostheses. It shall be emphasized once again that, in the context of the present invention, for the sake of simplicity, dental prostheses are covered by the term "tooth restoration parts".

The term "virtual tooth restoration" (referred to more briefly as "tooth restoration" in the following) is to be understood to cover corresponding electronic representations of tooth restorations, i.e. digital three-dimensional representations of such tooth restoration parts. To manufacture a tooth restoration part, for example, a CAD/CAM data set of the corresponding virtual tooth restoration can be forwarded to a manufacturing machine.

When treating a dental defect, a preparation of the teeth usually takes place, i.e. caries, old filling material or defective tooth parts are removed. What remains for each tooth is the remaining tooth structure, whose surface is divided into a prepared part (cavity) and an unprepared part. The boundary line between unprepared tooth surface and prepared tooth surface is referred to as the preparation line. In addition to the preparation lines, present only in the case of prepared teeth, each tooth also has at least one segmentation line, dividing a tooth from extradental structures such as gum and/or bone and/or adjacent teeth. A segmentation line is therefore an example of a further boundary line. It follows from these definitions that segmentation lines and/or preparation lines delimit unprepared tooth surfaces.

Knowledge of segmentation lines is also of primary importance in the field of orthodontics. Teeth can be separated from gum and neighboring teeth using these boundary lines, thus also enabling an orthodontic treatment plan in which, for example, the separated teeth can virtually be optimally aligned. For such an optimal dental alignment, knowledge of anatomical landmarks (incisor edges, cusps, fissures, etc.) and axes of the teeth is important.

In the context of the present invention, the term "geometrical analysis" of scan data can cover the segmentation of oral structures, the determination of segmentation lines and preparation lines, and also the determination of anatomical landmarks, tooth axes, directional terms, surface regions and further characteristic geometric structures. A geometrical analysis of radiological scan data can also cover a segmentation of the upper or lower jaw with the paths of nerves that belong to the teeth. This analysis is particularly important for the planning of dental implants. A geometrical analysis of scan data also covers the adjustment of geometrically deformable tooth models to the scan data. This adjustment process can be regarded as a preliminary measure for the actual geometric analysis.

Because of the complex structure of scan data, an interactive geometrical analysis with the aid of a graphical user interface is often difficult to carry out and time-consuming. Use of model-based processes can constitute an improvement, in which previous morphological knowledge about the teeth, perhaps also with their neighboring anatomical structures is used in the geometrical analysis.

Methods that allow a model-based segmentation of scan data are described primarily in the field of medicine. DE 103 57 206 B4 describes a dedicated segmentation method for human anatomical structures. Such approaches from the field of medicine cannot however be applied directly to the particular situation of dentistry, where teeth are often prepared, i.e. only parts of the teeth to be detected are present, and the scan data are usually optically generated owing to the necessity of great precision. For the data measured in this manner, the precise detection of segmentation lines and preparation lines is also particularly important.

It is an object of the present invention to provide a method and analysis system for the straightforward and reliable geometrical analysis of scan data of oral structures, which allows a satisfactory analysis to be performed quickly and with a low level of user interaction.

The object is achieved by a method according to claim 1, and by an analysis system according to claim 15.

In the context of the present invention, the fundamental terms "tooth type", "tooth model" and "preparation type" are to be understood in a very general manner. A tooth type is to be understood in the context of the invention as a very general possible grouping of teeth. For example a grouping can be done according to tooth number and/or age and/or abrasion and/or ethnicity and/or gender and/or according to morphological features (number of roots, number of cusps, etc.). The grouping can also be done according to whether a tooth can be assigned to the incisors, canines, pre-molars, molars, to the maxilla or the mandible. It is also possible to group teeth with different tooth numbers to a complex tooth type. It shall be emphasized here that, in practice, a grouping according to tooth number is preferred, i.e. tooth type and tooth number are synonymous.

Similarly, the term "tooth model" is used in a very general manner. A tooth model can comprise several partial models that describe, for example, anatomical structures such as tooth surfaces, gums, bone, nerve structures etc., as well as artificial structures such as implants, abutments, other anchoring systems, brackets, etc. Furthermore, a tooth model can also comprise boundary lines, anatomical landmarks, tooth axes, directional terms, surface regions and other characteristic geometric structures. It is important that at least those parts of the teeth are modeled that are required for the geometrical analysis of scan data. The remaining partial models preferably serve principally to stabilize the individualization procedure, since these can be adjusted to the corresponding structures in the scan data. The most important boundary lines are the segmentation lines and preparation lines already explained above. However, other boundary lines can also be used. For example, separation lines that separate adjustment areas from modeled artificial structures. The use of such lines serves, for example, for the detection of implant in the scan data. An implant partial model can, for example, be divided by a separation line into an active adjustment area outside of the jawbone, and an inactive adjustment area within the jawbone. Such an implant partial model can then be of use as a partial model of a tooth model in the geometrical analysis of the scan data.

In the context of the present invention, the term "preparation type" is also to be understood loosely. Besides the inlay, onlay, partial crown, crown, bridge and veneer preparation types, the term "tooth" can also be used as preparation type. The "tooth" preparation type serves in the description of a situation in which no preparation is yet present. This approach is in particularly expedient when the preparation type must be specified for each tooth in a scan data set. For example, several unprepared teeth may be present in a scan data set in addition to an inlay preparation and a crown preparation. These can then be described by the "tooth" preparation type. The "implant" preparation type is an important preparation type, particularly in the context of implantology. This can be used preferably in situations in which at least parts of implants are present in the scan data. For example, when specifying the "implant" preparation type for a tooth type, a corresponding tooth model can be used for the geometric analysis of scan data that contain an implant partial model. A further differentiation of the implant preparation type is possible by adding descriptors for the exact implant type. In that case an implant partial model of the physically present implant, for example in the form of a CAD data set, can be used in the geometrical analysis.

According to the invention, for the geometric analysis of scan data of oral structures a number of parameterized tooth models of desired tooth types is chosen according to the scan data to be analyzed, whereby the parameterization is performed on the basis of model parameters that comprise position parameters and/or shape parameters and line parameters, and whereby each tooth model comprises at lease one parameterized boundary line whose path is described by the line parameters and which divides a tooth model in at least one active adjustment area and at least one inactive adjustment area.

The tooth models available for geometric analysis can be stored in a model database. A selection of tooth models can then take place in such a way that the available tooth types of a model database are forwarded for selection to a selection unit, and the desired tooth types are selected with the aid of a selection signal, for example by the use of a graphical user interface. This selection can be made clear by the use of a graphical dental notation system. The extent of the tooth models used should preferably correspond to the extent of the scanned teeth, so that as much dental substance as possible can be analyzed using the method. In other words, several tooth models of different tooth types will usually be used for geometrical analysis. As an exception, however, a single tooth model can be selected.

In the process, preferably six position parameters of a tooth model describe the spatial position and orientation of a tooth model in the scan data. Anatomically meaningful shape variations of the tooth models are generated by parameterized geometric transformations that can differ from tooth model to tooth model and that are stored in the model database. In other words, the number of shape parameters can vary from tooth model to tooth model. Furthermore, in addition to the position and/or shape parameters and line parameters, the model parameters can comprise further parameters, that for example parameterize surface regions and/or material properties.

According to the invention, the tooth models and their boundary lines are adjusted to the scan data for individualization, whereby the individualization is carried out by variation of model parameters, and whereby the active adjustment areas of the tooth models are weighted to a greater extent than the inactive adjustment areas. "Individualization" is to be understood as the adjustment of tooth models to scan data, whereby individualization criteria, such as the adjustment of tooth models to suitable target structures in the scan data and/or the geometric interlinking of tooth models, should be complied with as far as possible.

The distinction made according to the invention between active and inactive adjustment areas in the adjustment of tooth models to scan data plays a central role. Normally, optical scan data do not comprise any parts below the gum, and interdental space is often only partially included owing to the optical measurement principle. The definition of adjustment areas according to the invention ensures that the entire active model range can be completely adjusted to the scan data. Model parts that do not have any counterpart in the scan data will be excluded by inactivation from the adjustment procedure, or weighted to a lesser extent. In this way, a significant stabilization of model individualization is achieved.

Finally, the scan data are segmented on the basis of the individualized tooth models with their individualized boundary lines, and/or at least one boundary line is determined in the scan data. The skilled person will be familiar with such methods. In principle, all the scan elements (e.g. vertices in the case of optical scan data, voxels in the case of radiological scan data) within the scan data that lie within the contour of a corresponding tooth model or a corresponding partial tooth model, or that differ from that by a certain difference value, can be selected and can optionally be assigned a segmentation number. The selection can be carried out in such a way that the respective scan elements are removed or that all remaining scan elements are removed, i.e. the respective scan elements are excised. Here, "partial tooth model" is to be understood as a part of an individualized tooth model, for example the occlusal surface. Any cavities present in the scan data are characterized in that the corresponding scan elements lie significantly within an individualized tooth model and are delimited by an individualized preparation line.

The determination of boundary lines in the scan data can be done by transferring the individualized boundary lines from the coordinate systems of the tooth models into the coordinate system of the scan data. A precision adjustment of the transferred boundary lines to the scan data can also optionally take place. In the case of optical scan data, for example, there may be small distances between the transferred segmentation lines and the measured surfaces in the scan data. Such a precision adjustment, in which for example the base points of the segmentation lines are adjusted to the measured surfaces, allows a precise determination of the segmentation lines in the scan data The method according to the invention allows the use of the tooth models with a reasonable computation effort and in an automated manner. In particular, owing to the specific construction of the tooth models, the method can be used for the automatic segmentation and/or determination of boundary lines. This is achieved by the stabilization of the individualization by simultaneously adjusting tooth models at a global level and adjusting boundary lines at a local level.

The independent claims and the following description contain particularly advantageous embodiments and further developments of the invention, whereby in particular the analysis system according to the invention can be adapted analogously to the features of the independent method claims. Furthermore, the various features of different embodiments can be combined in the context of the invention to give other embodiments.

Preferably, the individualization of tooth models is done by defining and solving an optimization problem. To solve the optimization problem, model parameters are varied until the optimization value is minimized, or an abort criterion is satisfied. The optimization value of the optimization problem may particularly preferably thereby comprise a number of optimization partial values that each correspond to certain desired individualization criteria. Preferably, this is done by computing a weighted sum of the optimization partial values. In this way, the weightings can control the influence of each individualization criterion. In this way, an optimization value is obtained for a model parameter set.

Preferred optimization partial values describe the adjustment of the tooth models to the teeth and/or to remaining tooth structure, i.e. the modeled tooth surfaces of the tooth model should be aligned as far as possible to the corresponding unprepared tooth surfaces of the scan data. To this end, a target structure in the scan data can be determined, for which the manner of computation depends primarily on the recording modality. The situation is particularly straightforward in the case of optical scan data, in which the measured surface can be used directly as a target structure. Determining the target structure is relatively easy in the case of CT/DVT scan data generated by X-rays. In this case, it is expedient to apply thresholding, in which the intensity values (measured in Hounsfield units) of each scan element are analyzed to determine whether they exceed a certain threshold. Radiologically dense structures, such as tooth structure and bone, can easily be selected in this way and used as target structures. Computation using MR scan data is more difficult, in which contour analysis is preferably applied on the basis of gradients of adjacent scan elements. For all modalities, the result is a surface target structure in the scan data, which can serve as a target structure for the tooth models. Preferably, information about local surface curvature is applied so that this target structure is particularly suitable for the individualization of segmentation lines and preparation lines. Suitable methods of computation will be known to the skilled person. Such knowledge of surface curvature has fundamental advantages for the individualization of boundary lines. After all, the segmentation lines and preparation lines of the scanned teeth distinguish themselves by connecting, in one line, scan elements with most pronounced concave or convex surface curvatures.

Further preferred optimization partial values described the adjustment of the tooth models to the opposing dentition and/or to static bite registrations and/or to dynamic bite registrations. When computing these optimization partial values, jaw motion may also optionally be considered. A further optimization partial value describes the adjustment of the tooth models to artificial oral structures, for example to implants or brackets. The corresponding target structures can usually be constructed by thresholding, particularly in the case of radiological CT/DVT scan data. A further individualization criterion concerns the mechanical stability of the tooth restorations that might arise from the tooth models and the scan data. The relevant optimization partial value preferably describes the mechanical stability of the tooth restorations and can therefore be used to assess the quality of the tooth preparations already carried out. In addition to those examples of functional individualization criteria, aesthetic individualization criteria, particularly relevant for incisor tooth restorations, can also be considered. The patient may prefer a particular shape (rectangular, triangular, square, shovel-shaped, etc.) for the upper incisors. The relevant optimization partial value can describe the discrepancy between the tooth model and the desired shape.

As explained above, several tooth types are usually selected for the geometrical analysis of scan data, so that groups of tooth models can then be individualized. To stabilize the individualization, it is advantageous to link tooth models within a group. Preferably, a further optimization partial value belongs to each linked group formed in this manner. Possible linked groups are, for example contact, position and shape groups, whose corresponding contact, position and shape optimization partial values describe the contact, position and shape relationships of the participating tooth models. Such linked groups allow, for example, the determination of tooth structure of a tooth type from the tooth structure of other tooth types, for example by linking the geometric shapes of tooth models. This is particularly important in the geometrical analysis of crown and bridge preparations.

For example, teeth 14 and 15 (using the usual FDI dental notation system) might be missing in the case of a bridge preparation, whereas teeth 13 and 16 are present and unprepared. Now, the problem is how to use the teeth on either side of the gap in order to arrive at the shape of the missing teeth. To this end, a "shape linkage group" of the tooth models for teeth 13 to 16 can be set up. During individualization of the tooth models, an adjustment of the tooth models for teeth 13 and 16 is made to the available tooth structure, which in turn is not possible in the case of teeth 14 and 15, since no corresponding tooth structure is available for the adjustment. In other words, the shapes of the tooth models for teeth 14 and 15 cannot be obtained directly from adjustment to the scan data. This problem is solved in the context of the invention in that, for example, the shapes of the tooth models for teeth 14 and 15 are indirectly obtained from the shapes of the tooth models of teeth 13 and 16. This can be achieved by considering, during individualization of the tooth models, a shape optimization partial value that describes the linking of the natural shapes of tooth models. By building a model database on the basis of proband scan data, the natural shape relationships of teeth are known. In the example mentioned above, for the tooth models for teeth 13 and 16, one can determine the proband scan data sets that best fit the tooth models for teeth 13 and 16. Subsequently, the corresponding proband tooth models for teeth 14 and 15 can be regarded as the desired tooth models for the bridge preparation. The shape optimization partial value then describes the shape deviation of the tooth models for teeth 14 and 15 to the proband tooth models for teeth 14 and 15.

The extent of the linkage group can be determined by any set of different tooth types from the set of desired tooth types (e.g. by tooth types 13 to 18, or e.g. by tooth types 15 and 26), i.e. the relevant tooth models need not necessarily be adjacent. Furthermore, a tooth model can also be assigned simultaneously to several linkage groups, e.g. to a shape linkage group and a contact linkage group.

If tooth models are adjacent, the adjacent tooth models are preferably linked to a "contact linkage group" in such a way that the relevant optimization partial value describes the contact situation of the adjacent tooth models. For example, the contact optimization partial value can result from the minimum distances of adjacent tooth models. In the case of a bridge preparation, for example, it is desirable that these distance values and therefore also the contact optimization partial value are null for the tooth models of the bridge, i.e. the tooth models of the relevant contact linkage group should touch each other at least at one point.

In addition to contact and shape linkage groups, "position linkage groups" can also be formed such that anatomically reasonable position relationships among the tooth models can be obtained during individualization. To this end, position parameters of a position linking group can define desired position relationships of the relevant tooth models. The optimization partial value of the relative positions of tooth model is preferably obtained from the spatial relationships of anatomical landmarks of the tooth models. In this way, the position parameters can describe desired relationships of the landmarks to each other, and the optimization partial value for the position relationships can be computed using the differences of those relationships. This can be illustrated by the alignment of the tooth model incisor edges in the anterior tooth region. Here, all relevant incisors may be regarded as members of a position linkage group. Even though the shapes of the tooth models may differ greatly here (rectangular, triangular, etc.), the requirement that the landmarks of the tooth model incisor edges must lie on a curve parameterized by the position parameters results in a favorable alignment of the tooth model incisor edges in the anterior tooth region.

The same applies to an optimization partial value that describes the spatial relationships of the shapes of tooth models. For example, a model database can be built using jaw scans of probands, whereby the tooth models generated from one jaw scan correspond to each other, since they originate from one proband. The optimization partial value for the linking of the shapes of the tooth models then preferably describes the discrepancies from the natural shape relationships of the tooth models within a linkage group. For example, for an initial tooth model that belongs to a shape linkage group, a proband tooth model that differs morphologically as little as possible from the initial tooth model of the shape linkage group, is determined using the model database. For this proband tooth model, the corresponding proband tooth models can then be determined, i.e. the tooth models originating from that same proband. Using the morphological deviations of the tooth model of the shape linkage group to the relevant corresponding proband tooth models, a so-called "correspondence deviation value" can then be computed for the initial tooth model of the shape linking group. This procedure is preferably repeated for each tooth model of the linkage group, and a determination of the optimization partial value for the shape relationships can be obtained from the corresponding deviation values.

The range of at least one linkage group should preferably correspond to the range of the scanned teeth, so that as many teeth as possible and/or as much residual tooth structure as possible is analyzed by the method. Particularly in the case of existing tooth preparations, the shape of the tooth restorations is deduced from the tooth structure and/or remaining tooth structure of all scanned teeth. The greater the tooth defect for a tooth type, the more important is the analysis of the tooth structure and/or remaining tooth structure of the other tooth types. However, particularly in the case of only a minor defect, for example in the case of an inlay preparation without any cusp involvement, the method according to the invention will work very effectively even with only a single tooth type. Alternatively, when several tooth types are used to analyze a situation with little or no defects, the linking optimization partial values can be weighted only slightly or with null values.

To stabilize the tooth model individualization, in a preferred embodiment of the invention the user can interactively label structures in the scan data, for which optimization partial values, describing the discrepancies from the labeled structures to corresponding structures in the tooth models, are computed. Important structures that may be labeled in the scan data are unprepared tooth surfaces, remaining tooth structure, segmentation lines or preparation lines of scanned teeth, anatomical landmarks, artificial oral structures, contact points to adjacent teeth and contact points to the opposing dentition. The individualization is then stabilized by minimizing the distances of the labeled structures to the corresponding structures of the tooth models during optimization. This approach is particularly applicable in the case of significant deviations from the norm in the scanned teeth, or in their relative positions to each other. Equally, measurement artifacts may be present in the scan data, or the path of preparation lines may not be clearly defined owing to a poorly executed preparation.

The interactive labeling of structures in the scan data to assist the individualization procedure is preferably done using mouse input of a graphical user interface. The type of structure to be labeled depends greatly on the individualization criterion, whereby the manner in which the optimization partial value is computed is very similar for all individualization criteria with user interaction. To compute the optimization partial value, in a preferred embodiment minimum distances are computed from the structures labeled in the scan data to the corresponding structures in the tooth models. An optimization partial value is then obtained from the sum of the squares of such distances.

In a preferred embodiment of the method, after determining the individualized tooth models and prior to the subsequent geometrical analysis of the scan data, a precision adjustment of the individualized tooth models with their individualized boundary lines with respect to each other and/or to the scan data is carried out. This is advantageous, since the shape diversity of the tooth models with their boundary lines is effectively limited by the number of shape parameters or line parameters, and since the preparation lines in particular should be computed with great precision. It is advantageous to apply deformation transformations that carry out a precision adjustment with as few displacement values as possible and thereby do not induce edges or folds. These adjustments can be carried out analogously to the individualization of the tooth models, whereby the parameters of these deformation transformation are used here as optimization partial values. The computation of the optimization partial value to be minimized from optimization partial values can be applied unaltered.

The geometrically deformable tooth models in a model database can be built up according to various principles. Since the target structures in the scan data are mostly boundary surfaces, surface models lend themselves to be used as tooth models. The geometric modeling of the model surfaces can be performed by simple triangulation, or by using mode complex higher-order modeling techniques (Bezier models, non-uniform rational B-spline models, B-spline models, etc.). Compared to surface models, the use of volume models (voxel models, finite-element models, etc.) involves more computation effort and storage. These allow a good modeling of inner dental structures as well as mechanical properties. It is advantageous to label anatomical landmarks, tooth axes, directional terms, surface regions and/or other characteristic geometric structures on the tooth models, since these labels can be transferred to the scan data after successful individualization of the tooth models. A measuring of the scan data can also be carried out on the basis of these individualized geometric structures.

The tooth models of a model database can be present in various resolutions. It is then advantageous to first carry out the method according to the invention on the tooth models with the lowest resolution level whereby, after a successful run, the resolution level is increased in later stages. This primarily increases the speed of the method. The database can, for example, also comprise complete sets of tooth models in various levels of resolution. After a complete optimization, i.e. after the individualization of tooth models from a database or partial database with a low resolution level, the method is then carried out again with a database or partial database that has a higher resolution. The individualized tooth models of a previous run can be used as initial models for the next run. Equally, it is possible to work at various levels of resolution when solving the optimization problem.

The geometric transformations of tooth model are described by shape parameters, whereby this parameterization can be realized in various ways. Preferably, transformations are used in which the shape parameters of the tooth models are sorted according to their influence on the tooth model geometry. In other words, the important shape parameters are at the top of the shape parameter list, and will be optimized first during tooth model individualization, before optimizing shape parameters that parameterize tooth model details. In this way, an increase in speed and stabilization of the tooth model individualization is achieved. The domain of definition of the shape parameters is preferably not arbitrary, but is preferably determined by the analysis of training data. In this way, it can be achieved that only anatomically pertinent tooth models are generated by the shape parameters.

The use of parameterized three-dimensional transformation fields for the tooth models is particularly advantageous for the method proposed according to the invention. A three-dimensional transformation field comprises displacement vectors for the vertices (support points) of a tooth model. These displacement vectors can also be parameterized, for example by the parameterized displacements of anatomical landmarks of a tooth model.

The displacement vectors of all vertices are then obtained, for example, from the distances of the vertices to the displaced anatomical landmarks. In applying the method according to the invention when a quick result is more important than precision, it is advantageous to use shape parameters that correspond to geometrical construction parameters (e.g. tooth width, tooth depth, cusp distance, incisor edge thickness, root length, etc.).

A further preferred embodiment of the method according to the invention is characterized in that the boundary lines lie on the surfaces of the tooth models and/or that the boundary lines have a parameterized distance to the surfaces of the tooth models and/or that the line parameters are chosen such that the boundary lines do not intersect and/or maintain a minimum distance to each other. The possibility that the boundary lines have a parameterized distance to the surfaces of the tooth models increases the boundary line path variety. This approach is particularly expedient when using tooth models of a model database that was created by analyzing a relatively small set of proband scan data. It should be noted that the vertices of a boundary line can usually comprise several distances to the corresponding tooth model. It is advantageous to specify a maximum distance value in order to limit the distances and/or to compute an optimization partial value, which is obtained from the distance values. A reasonable limitation of the line parameters is achieved by specifying, in the optimization procedure, the constraint that the boundary lines do not intersect and/or that they maintain a minimum distance to each other. For a prepared tooth, the preparation line generally lies above the segmentation line, or may at most touch it in special cases. The consideration of these constraints leads to a stabilization of the tooth model individualization.

In a particularly preferred embodiment of the method, the boundary lines of a tooth model comprise at least on segmentation line and/or at least one preparation line. In the case of optical scan data, the most important segmentation line describes the transition from tooth structure to gum, which transition is usually characterized by a concave surface curvature. In the case of radiological scan data, in addition to this segmentation line, a segmentation line that describes the transition from tooth structure to jawbone can be used, whereby this transition is also characterized by concave surface curvatures. Further segmentation lines can describe the contact to adjacent teeth. Where there is no contact, such a segmentation line can devolve into a point, so that the corresponding enclosed inactive adjustment area has a surface area of null. In orthodontic problems, the scan data may also contain brackets. In that case it is advantageous to describe the contact surfaces of the brackets to the teeth using corresponding segmentation lines. Here also, the transition from tooth structure to the brackets is characterized by concave surface curvatures.

In the analysis of scan data of prepared teeth, the use of preparation lines that delimit the cavities of prepared teeth can be of prime importance. In contrast to the segmentation lines described above, the transition from unprepared tooth structure to a cavity is characterized by convex surface curvatures. Owing to these relationships, for the individualization of the boundary lines, target structures that exhibit corresponding surface curvatures are preferably determined in the scan data. For the individualization of the segmentation lines, a segmentation line target structure is determined that consists of scan data parts and comprises at least one concave surface structure. In contrast, for the individualization of the preparation lines, a preparation line target structure is determined that consists of scan data parts and comprises at least one convex surface structure.

Preferably, in a further preferred embodiment of the method, the adjustment areas lie on the tooth model surfaces, and the active adjustment areas are adjusted to unprepared tooth surfaces in the scan data in the case of optical scan data, and, in the case of radiological scan data, to unprepared tooth surfaces that lie outside the gum or jawbone or that comprise enamel. It is thereby irrelevant, whether the used tooth models are surface models or volume models. It is only important that the active adjustment areas are surface regions of the tooth models and correspond to unprepared tooth surfaces in the scan data. In other words, the active adjustment areas should preferably, during individualization, be adjusted as completely as possible to all existing unprepared tooth surfaces in the scan data. After successful individualization of the tooth models, the individualized active adjustment areas then correspond to the unprepared tooth surfaces. The extents of the active adjustment areas are defined by parameterized boundary lines, wherein the boundary lines are to be chosen such that they are adjusted during individualization to target structures in the scan data that border unprepared tooth surfaces. In the case of optical scan data, these target structures comprise, for example, the concave transition from gum to unprepared tooth surface, and the convex transition from cavity to unprepared tooth surface. In the case of radiological scan data, the transition from jaw bone to unprepared tooth structure can be used as a concave transition, as can the transition from enamel to dentine in the neck of a tooth. The distinction between enamel and dentine can be made, for example using the Hounsfield values of the scan elements.

A further preferred embodiment of the method according to the invention is characterized by the computation of a quality value for the individualization of tooth models, which is obtained from a number of quality values that describe compliance with individualization criteria. The quality value of an individualization then quantitatively describes how well the relevant individualization criteria were complied with. A quality value of 100% should be used for the individualization of tooth models for which all individualization criteria were completely complied with. Smaller percentages denote individualizations in which certain individualization criteria are only partially complied with, or not at all. For example, an individualized tooth model can still, at the end of the procedure, comprise a deviation between the tooth model surface and the scan data. A quality value can then be computed by applying a non-linear conversion to the mean deviation of the tooth model surface vertices. A conversion table can be used, for instance, in which mean deviation values are associated with quality partial values. A mean deviation value should correspond to a quality partial value of 100%, and mean deviation values that exceed a relatively large threshold (e.g. 1 cm) should correspond to quality partial values of 0%. The computation of a quality value from quality partial values can preferably be done by computing a weighted sum of the quality partial values. The weighting factors allow the influence of each individualization criterion to be controlled. Preferably, the weighting factors are chosen such that all individualization criteria can be considered equally well.

As long as the individualization of the tooth models is performed by solving an optimization problem, the quality partial values can preferably be determined from the optimization partial values, whereby both values belong to the same individualization criterion. A quality value can be determined from the corresponding optimization partial value by a generally non-linear conversion. A minimum possible optimization partial value corresponds in this case to a quality partial value of 100%, and a maximum possible optimization partial value to a quality partial value of 0%.

A optimization partial value can in principle also be regarded directly as a quality partial values. An advantage in the use of converted quality partial values compared to the use of unaltered optimization partial values is the better visualization for the user. It is more understandable to speak of a 85% adjustment of a tooth model to the tooth structure or remaining tooth structure, that to speak of a mean distance value of 158 µm of the tooth model vertices to the tooth structure or remaining tooth structure. Therefore, in the following, the term "quality partial value" is used, even when it can comprise an optimization partial value, unless explicitly stated otherwise.

The quality partial values (or the relevant optimization partial values) preferably determine whether the user should be prompted to label structures in the scan data, for use in the individualization of tooth models in a repeated method run. For example, if the quality partial values for the adjustment of a tooth model to the tooth and/or remaining tooth structure lie below a predefined threshold (or above when optimization partial values are used as quality partial values), the user will be prompted to label the relevant tooth or remaining tooth structure. The labeling yields a new individualization criterion, namely the adjustment to this label of a tooth model belonging to that label. Subsequently, the method according to the invention is started again, and it is checked whether all individualization criteria—including the new individualization criteria—are satisfied to a satisfactory quality and whether any more user input is required. This approach is preferably performed iteratively until an abort criterion is satisfied. Such an abort criterion can be, for example, that all quality partial values have exceeded a threshold (or fallen below a threshold), or whether a predefined number of iterations has been reached.

The weighting of adjustment areas of the tooth models can be constant during individualization, or can be altered during the individualization procedure. One version of the method is characterized in that the weighting of the adjustment areas for a tooth model is performed on the basis of the quality partial values for the individualization of boundary lines, whereby, with increasing quality partial values for the individualization of boundary lines, the active adjustment areas are weighted more heavily in the adjustment to the scan data. This approach is particularly advantageous when the individualization procedure commences with tooth models positioned in the scan data that exhibit great differences to corresponding target structures in the scan data. In such a case, the boundary lines are also usually not yet adjusted very well to the scan data. In other words, the active adjustment areas of the tooth models can differ in extent quite markedly from the unprepared tooth surfaces in the scan data. Only when the boundary lines are relatively well adjusted to the scan data, expressed as a correspondingly high quality partial value for the individualization of the boundary lines, is it safe to assume that the active adjustment areas also correspond relatively well to the unprepared tooth surfaces. It is expedient then to weight these adjustment areas more heavily during individualization.

Another version of the method is characterized in that anatomical landmarks and/or tooth axes and/or directional terms and/or surface regions and/or other characteristic geometric structures are labeled on the tooth models and transferred to the scan data after individualization, and/or a geometric measurement of the scan data is performed on the basis of these individualized structures. The labeling procedure can be done interactively or algorithmically. In an interactive method, it is advantageous to use a graphical user interface to generate the labels. It is more time-saving and preferable to use suitable algorithms to label characteristic geometric structures on the tooth models. Such methods are known to the skilled person. An approach in which the labels are algorithmically determined, after individualization of the tooth models and prior to transferring to the scan data, is particularly preferred. This approach allows a precise determination of characteristic geometric structures in the scan data, even when the geometrically deformable tooth models alter their characteristic morphology during the individualization procedure.

In a particularly preferred embodiment of the method according to the invention, virtual tooth restorations of prepared teeth are determined from the individualized tooth models and scan data. Preferably, the preparation types of the teeth corresponding to the tooth models can be determined from the characteristic geometric shapes of the determined virtual tooth restorations and/or from the individualized boundary lines corresponding to the individualized tooth models. Optionally, for these determined preparation types, verbal or symbolic descriptors can be displayed with a dental notation system and/or a reduced dental notation system and/or graphically with the scan data.

Suitable methods for determining virtual tooth restorations from individualized tooth models and scan data will be known to the skilled person. Basically, the preparation lines of the scan data are joined to the corresponding tooth models in a suitable manner, as continually and smoothly as possible, and the cavities of the prepared teeth are then added as lower boundaries. The result for the virtual tooth restorations are three-dimensional models of milling objects that can be manufactured by machining. The virtual tooth restorations can also be formed in a segmented manner, by determining a supporting structure first and then an upper structure with the occlusal surfaces.

The preparation types of the scanned teeth can also be determined from the individualized tooth models with their individualized boundary lines and/or the corresponding virtual tooth restorations. The simplest case is when no preparation lines have been detected for a tooth type; in this case the relevant tooth is not prepared and no cavity is present. In the context of the invention, owing to these relationships, the "tooth" preparation type is used for a missing preparation in addition to the inlay, crown, etc. preparation types. In the case of existing preparations, on the other hand, the preparation types (inlay, crown, bridge . . . ) of the scanned prepared teeth are deduced from the characteristic geometric shapes of the determined virtual tooth restorations and/or the corresponding individualized boundary lines.

In a method according to the invention to generate a model database that contains a number of parameterized tooth models (i.e. at least one tooth model) for each of several tooth types, for use in the method described above, the parameterization is carried out by applying model parameters that comprise position parameters and/or shape parameters and/or line parameters, and whereby each tooth model comprises at least one parameterized boundary line whose path is described by the line parameters and which separates a tooth model in at least one active and at least one inactive adjustment area.

In a preferred embodiment of the method according to the invention for the building of a modal database, the entire model database or at least parts of the model database are built by analyzing a set of optical and/or radiological scan data of artificial and/or natural oral structures. In the context of the invention, artificial oral structures are to be understood as artificial teeth or groups of teeth, dentures and also implants, abutments and other anchoring systems. Usually, such artificial oral structures are available in a multitude of ready-to-use versions from various commercial suppliers. On the other hand, in the context of the invention, natural oral structures comprise natural teeth or groups of teeth, dentition and also gum, jawbone, nerves and other anatomical structures. Preferably, the optical scan data of natural oral structures are obtained from optical scans of plaster casts of caries-free and defect-free upper and lower jaws. Of course, radiological scan data of jaws can also be used, whereby such scan data are less precise that optical scan data, but comprise subgingival and intradental structures. A model database built up on the basis of CT/DVT scans allows the modeling of tooth models that comprise root structures. Such tooth models are then preferably suitable for the geometrical analysis of radiological scan data.

Usually, the scan data must first be segmented in order to obtain scan data of a desired tooth type in a first database building step, especially in the case of scan data of natural oral structures. This step is usually dispensed with in the case of scan data of artificial oral structures, since these are usually provided in a physically separated manner and can be scanned individually. In both cases, the result of the measurement of physically existing oral structures is a scan data set for a desired tooth type, which can be used in the building of a model database. Insofar as both optical as well as radiological scan data of the individual probands are available, it is advantageous to combine both scan data types after segmentation in the building of a model database. To this end, pairs of optical and radiological scan data are preferably identified for the same tooth type of one proband, and these are noted. This can be achieved by aligning both scan data sets of a pair as far as possible, by determining optimal translation and rotation values. This yields combined optical-radiological scan data sets that are equally suitable for the building of a model database. The tooth models constructed in this way combine the high accuracy of optically measured tooth surfaces with radiologically measured subgingival structures.

In the following second step of database building, the tooth models of a tooth type can be constructed, i.e. an adjustment takes place of surface tooth models or volume tooth models (of a desired resolution) to the scan data of a desired tooth type. If a segmentation was carried out in the first step of database building, the segmentation lines are generally known in the scan data, and these can be transferred to the tooth models after construction. Alternatively, an interactive labeling of the segmentation lines on the tooth models can take place. Optionally, anatomical landmarks, tooth axes, directional terms, surface regions and/or other characteristic geometric structures can be determined algorithmically and/or interactively for the tooth model in this step of database building. The necessary techniques will be known to the skilled person.

An analysis of morphological differences between the tooth models of a tooth type can be carried out in a third step of database building, by calculating a morphological difference value for each possible tooth model pair. This can be achieved by bringing both tooth models of a pair into alignment as far as possible, by determining optimal translation and rotation values, and that the morphological difference value describes the remaining morphological difference between the two tooth models.

In a fourth database building step, a mean tooth model of a tooth type can be selected by analyzing the computed morphological difference values. On the basis of the difference analysis of the tooth models relative to each other, (n−1) morphological difference values are obtained for each of the n tooth models of a tooth type. The tooth model with the minimum sum of squares of the morphological difference values is preferably regarded as the mean tooth model.

A sorting of the tooth models of a tooth type can then preferably be performed in a fifth database building step. The sorting is generated particularly preferably in that, starting with the mean tooth model of the tooth type, the remaining tooth models of the tooth types are added to the sorting on the basis of morphological difference values to the already sorted tooth models. Preferably, the tooth model whose sum of squares of morphological difference values is maximum compared to the already sorted tooth models is added to the sorting. This approach ensures that those tooth models that differ most on account of their morphology appear at the start of the sorting.

In a final sixth step of database building, a geometrical transformation is preferably added to the mean tooth model of a tooth type, on order to generate intermediate shapes of tooth models for the individualization. A suitable geometrical transformation for a mean tooth model is preferably defined by the constraint that the shape of the mean tooth model can be transferred smoothly to at least one target tooth model coming afterwards in the sorting. This approach ensures that the applicable shape parameters can be variegated effectively and that, with an increasing number of shape parameters, the shape variety of the transformed mean tooth model is increased. The number of target tooth models can depend on the purpose of the model database. Since the tooth models having the greatest morphological differences appear at the start of the sorting, a reduction of the storage requirements of the model database can be achieved by considering a relatively small number of target tooth models. For example, in a geometric analysis of scan data in which speed is more important, geometric transformations of mean tooth models can be used, that have been developed from a smaller number of target tooth models. The associated memory requirements for the geometrical transformations are then relatively small.

To carry out the method, an analysis system according to the invention for the geometrical analysis of scan data of oral structures requires an interface for receiving scan data measured by a modality; a selection unit for selecting the tooth types to be used by the method; a memory module with a model database that comprises a number of parameterized tooth models for each of various tooth types, whereby the parameterization is performed using model parameters comprising position and/or shape parameters and line parameters, and whereby each tooth model comprises at least one parameterized boundary line whose path is described by the line parameters and which divides a tooth model in at least one active adjustment area and at least one inactive adjustment area. The analysis system also requires an individualization unit in which the tooth models and their boundary lines are adjusted to the scan data for individualization, whereby this individualization is performed by the varying of model parameters and whereby the active adjustment areas of the tooth models are weighted more heavily than the inactive adjustment areas. Finally, the analysis system requires an analysis unit in which the scan data are segmented on the basis of the individualized tooth models with their individualized boundary lines and/or in which at least one boundary line is determined in the scan data.

The selection, individualization and analysis units of the analysis system can particularly preferably be realized in the form of software on a suitable processor of a computer. This computer should comprise an appropriate interface for receiving scan data and a suitable memory module for a model database. The memory module need not be an integral part of the computer, and it is enough for the computer to be able to access a suitable external memory module. A realization of the method according to the invention in the form of software has the advantage that existing analysis systems can be upgraded relatively easily by suitable updates. In particular, an analysis system according to the invention can also be a control unit for the modality that records the scan data, having the necessary components for the processing of the scan data according to the invention.

The invention will be described in the following using the exemplary embodiments and with reference to the drawings:

FIG. 3 shows a two-dimensional schematic representation of scan data D of teeth T13 to T18 with individualized tooth models M;

FIG. 4 shows a two-dimensional schematic representation of scan data D of teeth T13 to T18 with tooth restorations R and determined preparation types (inlay, crown, bridge, tooth);

Figure 19:
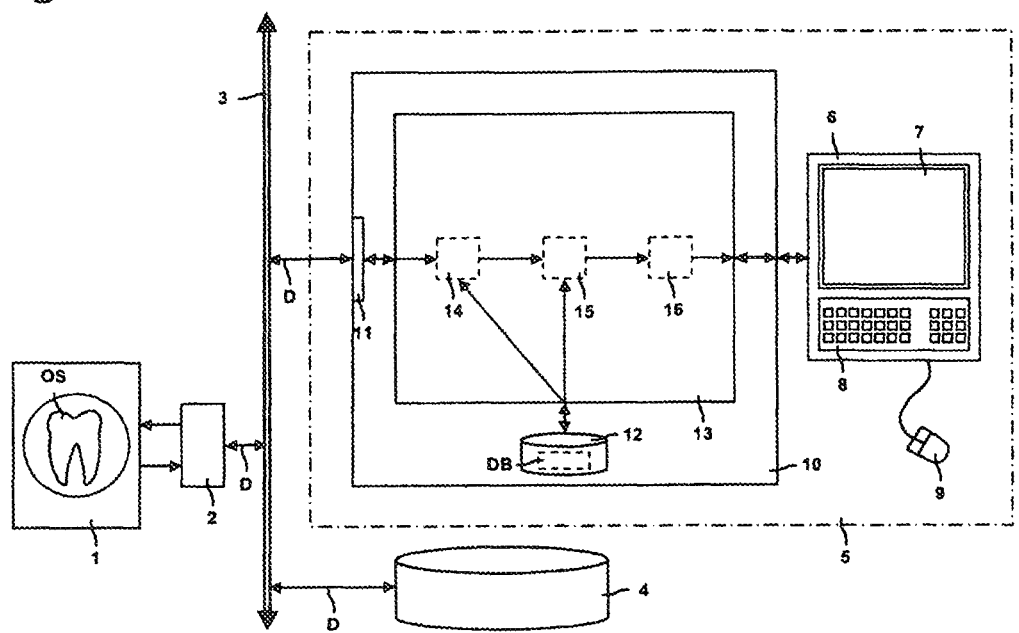
FIG. 19 shows a schematic representation of an embodiment of an analysis system according to the invention.

The exemplary embodiment of an analysis system 5 according to the invention, schematically shown in FIG. 19, essentially comprises a computer 19 to which is connected a console 6 or similar with a display 7, a keyboard 8 and a pointer device, in this case a mouse 9. The computer 10 can comprise a conventional computer realized in the usual manner, for example a PC or a workstation, which can be otherwise used for data processing and/or for the control of imaging devices (modalities) such as optical scanners, computer tomographs, digital volume tomographs, etc. Essential components of this computer 10 are, amongst others, a central processor 13 and an interface 11 for the receiving of scan data D of oral structures OS that were measured by a modality 1, in this case an optical scanner.

In the embodiment shown in FIG. 19, the modality 1 is connected to a control unit 2, which in turn is connected with a data bus 3 to which the analysis system 5 is also connected. Furthermore, a mass storage device 4 for the interim storage or permanent storage of scan data D recorded by the modality 1 and/or scan data D processed by the analysis system 5 is also connected to the data bus 3. Of course, any number of components such as further modalities, mass storage devices, workstations, output devices such as printers, filming stations, milling units or similar can be connected to the data bus 3 forming a larger network. Equally, a connection to an external network or further analysis system is possible. All scan data D are preferably formatted in the so-called STL standard (STL=Surface Tesselation Language) and/or in the DICOM standard (DICOM=Digital Imaging and Communication in Medicine).

Control of the modality 1 is performed in the usual manner via the control unit 2, which also acquires the data from the modality 1. For on-site control, the control unit 2 can comprise an own console or similar (not shown here). It is also possible for control to be performed for example via the data bus, using a separate computer located in the vicinity of the modality.

Initially, in a first process step, the scan data D are selected and the extent of the tooth types to be used by the method is determined. The scan data D can for example be forwarded from the modality 1 or its control unit 2 directly to the computer 10 via the data bus 3. The scan data D can also have been recorded previously and stored in a mass storage device 4. In the embodiment described in the following, it is assumed that the scan data D to be analyzed are optical, not radiological, scan data D. A geometrical analysis of radiological scan data D proceeds analogously to an analysis of optical scan data D. One difference lies in the determination of target structures for the tooth models. For optical scan data D, the target structures are given by the measured surfaces or parts of these surfaces. In contrast, for radiological scan data D, suitable surfaces are usually generated in advance using methods known to the skilled person. For example, by triangulation methods or contour analysis methods, the surfaces of teeth and/or gums and/or jaw bone can be obtained from CT/DVT scan data sets in a triangulated form. Based on this surface information, the geometrical analysis of the radiological scan data D can be carried out analogously to the geometrical analysis of optical scan data D.

Figures 11, 12, 13, 14:
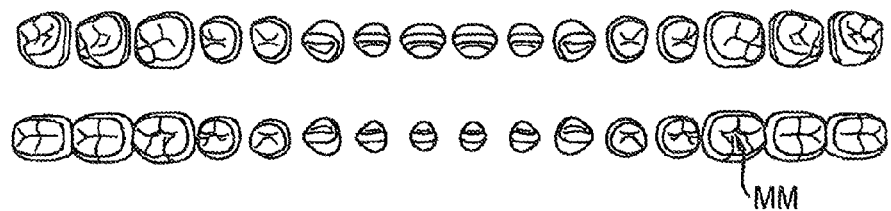
FIG. 11 shows a perspective view of mean tooth models MM of a model database for tooth types 18 to 48.
FIG. 12 shows a representation of a dental notation system with which the tooth types to be used in the method are defined.
FIG. 13 shows a representation of a dental notation system with which the preparation types determined by the method are depicted.
FIG. 14 shows a reduced representation of the dental notation system of FIG. 13.

The extent of the tooth models to be used by the process is preferably determined by specifying a number of different tooth types. Optionally, the user can also specify the preparation types of the selected tooth types. These specified preparation types can then, for process control purposes, be compared to the determined preparation types or may also be used in the computation of optimization partial values. For example, in the case of crown or bridge preparations, the occlusion surfaces of the corresponding tooth models outside of gum or residual tooth structure should lie in the scan data D. For better clarity for the user, these specifications can be done using a graphical user interface and a dental notation system, for which an example is shown in FIG. 12. The corresponding mean value tooth models of tooth types number 18 to number 48 are shown in FIG. 11. Preferably, the range of the tooth types to be used should correspond to the extent of the tooth types of the scanned teeth. In the following, it is assumed that the user has selected several tooth types with the corresponding preparation types (cf. FIG. 13). In this case, application of the variant of the method according to the invention, in which groups of tooth models are individualized, is appropriate. However, the preparation types can be displayed using a reduced dental notation system (cf. FIG. 14) or graphically with the scan data (cf. FIG. 4). This diagram also shows the tooth restoration determined from the individualized tooth models and the scan data D.

The selection of tooth models from a model data base DB can take place using a selection unit 14, realized here in the form of a software model on the processor 13 of the computer 10 (cf. FIG. 19). The model database DB is stored for example in a memory 12 of the computer 10, to which the selection unit 14 has access, or the selection unit 14 can determine selection settings, which are considered by subsequent processing modules during model individualization.

Figure 1:
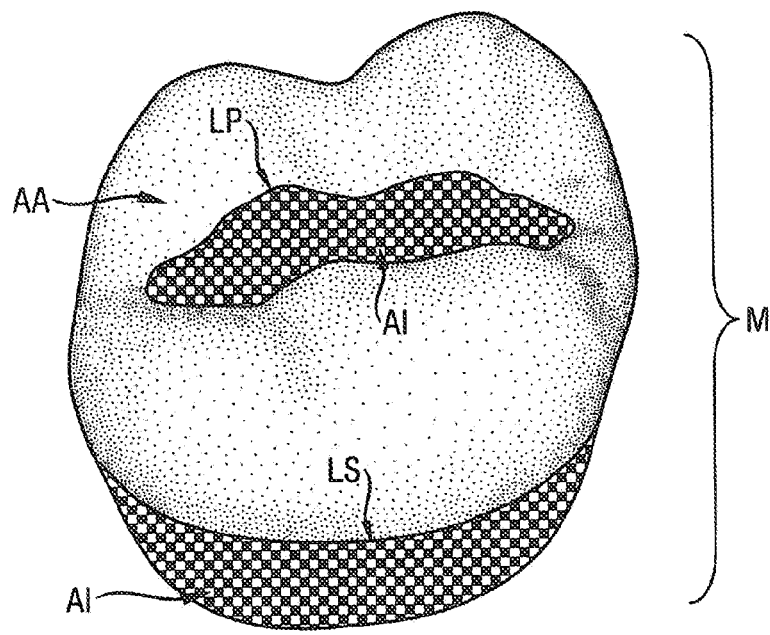
FIG. 1 shows a perspective view of a tooth model M with boundary lines LS, LP and an active adjustment area AA and two inactive adjustment areas AI.

FIG. 1 shows an embodiment for a 16-tooth model M. The surface tooth model M comprises a segmentation line LS and a preparation line LP. These two boundary lines LS, LP define an active adjustment area AA and two inactive adjustment areas AI. In this embodiment, the boundary lines LS, LP lie on the surface of the tooth model M. Since optical scan data were assumed for the embodiment described above, the use of surface models is expedient for the geometrical analysis. Furthermore, the tooth model M shown in FIG. 1 does not comprise any partial model, such as for example an implant partial model. Parameterization of the boundary lines LS, LP can be done using known computer graphics texture coordinates of the tooth model M. Two-dimensional texture coordinates can be assigned to each vertex of the tooth model M. The vertices of the boundary lines LS, LP then ensue from a set of two-dimensional texture coordinates. These texture coordinates can be used as line parameters of the tooth model M in this example.

The determination of individualized tooth models for the desired tooth types is achieved in the embodiment described above by solving an optimization problem, whereby an optimization procedure is carried out, commencing with initial tooth models of the desired tooth types. In the individualization of tooth models, the initial tooth models are first determined for the desired tooth types. Preferably, the initial tooth models are stored in the model database and are particularly preferred mean tooth models of the desired tooth types. However, initial tooth models can also be used that arise from corresponding individualized tooth models of a previous application of the method according to the invention.

After selecting the initial tooth models, these should be roughly positioned relative to the scan data before adjusting to the scan data, i.e. a pre-positioning of the initial tooth models is carried out. In the case of radiological scan data (e.g. CT/DVT scan data), directional terms (anterior, posterior, etc.) of the data set are usually known, and the recorded volume usually comprises the oral cavity with adjacent structures. The situation in the case of an optical jaw scan is similar. In that case also, direction conventions for the scan data are usually complied with. The occlusion surfaces of the teeth show a defined axial direction and the roughly parabolic dental arches open into a further defined axial direction. In the case of intra-oral optical scans, the situation is slightly different. Here also, the occlusion surfaces of the teeth are oriented in a defined axial direction and directional terms (e.g. mesial, distal) apply to the ends of the measured parts of a dental arch. On the basis of this implicit direction information and the known measurements of the scan data, the initial tooth models can be positioned relative to the scan data before commencing with the method.

Subsequently, the tooth models are adjusted to the scan data by varying model parameters. FIG. 3 shows exemplary scan data D with individualized tooth models M for typical inlay, crown and bridge preparations.

The individualization of tooth models is preferably carried out by solving an optimization problem, in which the optimization value ensues from a number of optimization partial values that correspond to desired individualization criteria, of which several will be explained again below. After their computation, the individual optimization partial values are combined to a single optimization value. This is preferably done by computing a weighted sum of the optimization partial values. In this way, the weighting factors allow a control of the influence of each of the individualization criteria. For example, a greater weighting factor for the adjustment of tooth model surfaces to the teeth or remaining tooth structure, together with a lower weighting factor for the adjustment of the boundary lines to corresponding target structures, can lead to individualized tooth models that are very well adjusted to the teeth or remaining tooth structure, but which do not comprise a 100% adjustment of the boundary lines to the corresponding target structures. Preferably, the weighting factors are chosen such that all individualization criteria can be complied with equally. The solution to the generally non-linear optimization problem can be performed using techniques known to the skilled person. One straightforward possibility is the determination of the minimum optimization value by gradient descent.

An important optimization partial value describes the adjustment of a tooth model to the corresponding tooth structure and/or residual tooth structure in the scan data. The determination of a corresponding target structure depends primarily on the recording modality of the scan data. In the embodiment shown here, optical scan data are used and the measured surface is used directly as a target structure. Computation of the optimization partial value is preferably done by obtaining the sum of squares of the distances between tooth model vertices of the tooth model and the target structure. In the same way, computation of the optimization partial value for the adjustment of the boundary lines of a tooth model to structures in the scan data is performed with corresponding surface curvatures. Scan elements whose concave surface curvature lies above a threshold value can for example be used as target structure for the segmentation lines. A target structure for preparation lines can contain, for example, scan elements with convex surface curvatures above a corresponding threshold value. The vertices of the active adjustment areas can be weighting stronger than the inactive adjustment areas in the context of the different weighting, according to the invention, of active and inactive areas. In particular, it is possible to only use the vertices of the active adjustment areas in the computation of the optimization partial values, i.e. the vertices of the inactive adjustment areas are weighed with zero. The minimum distances between tooth model vertices and target structure can be used as distance values, or the distances along the surface normals of the tooth model vertices to the target structure could equally be used.

A further important optimization partial value describes the contact of a tooth model to the opposing dentition in the above example. The opposing dentition is measured directly or indirectly using a bite registration. In both cases, so-called antagonist data are obtained. Use of prefixed distance values are recommended for describing the contact situation of a tooth model to a corresponding antagonist. A negative prefix for a distance value of a tooth model vertex occurs when it lies within the antagonist, otherwise its prefix is positive.

If the minimum distance value is now determined, a single prefixed contact distance value is obtained for a tooth model. If this value if positive, no intersection is present; a value of zero indicates one or more contact points; a negative value indicates an intersection. The optimization partial value for the contact of a tooth model to the opposing dentition is then preferably the square of the contact distance value.

A linking of tooth models is preferably considered by optimization partial values that describe the contacts and/or the spatial relationships of the positions and/or the spatial relationships of the shapes of the linked tooth models. In the example described above, the tooth types 13 to 18 were selected by the user (cf. FIG. 13). The six neighboring teeth can then form a contact-linking group for the contact of tooth models. An optimization partial value for the contact of the tooth models to each other can be computed in a completely analogous manner to the suggested computation for describing contact to opposing dentition. To this end, preferably five contact distance values are computed for the six tooth models, and the contact optimization partial value is then given by the sum of the squares of these contact distance values.

In the above example, the extent of the position linking group corresponds to the extent of the contact linkage group. The corresponding position optimization partial value can be computed on the basis of the spatial relationships of anatomical landmarks of the linked tooth models. Determination of suitable landmarks preferably takes place during building of a model database and can be carried out interactively and/or algorithmically. A suggested manner of computation of the optimization partial value assumes that anatomical landmarks of linked tooth models should lied on parameterized three-dimensional curves. The sum of squares of the distance values between the landmarks and the curves is then preferably calculated as position optimization partial value. A curve known to the skilled person is the Curve of Spee, upon which the incisor edges and cusps of the upper teeth should lie.

A further linking optimization partial value describes the spatial interrelationships of the shapes of linked tooth models. In the above example, the corresponding shape linkage group is once again formed by the six tooth models 13 to 18. To compute the shape optimization partial value, it is assumed in the above example that the model database used was built on the basis of scan data of a representative set of probands. Those tooth models of other tooth types that originate from the same proband then correspond to a model database tooth model of a tooth type. Tooth models of the other tooth types, originating from the same proband, correspond in that case to a tooth model of a tooth type. The shape optimization partial value for the linking of shapes of tooth models is then preferably obtained by computing the variance of the tooth model correspondences.

To this end, a proband tooth model is specified from the model database for each tooth model of the shape linkage group, referred to in the following as the initial tooth model. The association of an initial tooth model to a proband tooth model of the same tooth type can be done using the shape parameters of the initial tooth model. When building the model database, such shape parameters of the geometrical transformation of the mean tooth model that optimally describe the proband tooth model are determined for each proband tooth model. These shape parameters are referred to in the following as proband shape parameters and are preferably stored in the model database. Subsequently, the proband tooth model, for which the proband shape parameters differ least from the initial shape parameters of the initial tooth model, is assigned to an initial tooth model with an initial shape parameter set. For example, the differences between the initial shape parameter set to all proband shape parameters can first be computed. The minimum of the least squares of these differences then defines the desired proband shape parameter set. The corresponding proband tooth models in the model database can then be determined for the proband tooth model determined in this manner. To this end, only the shape parameters of the proband tooth models need to have been stored in the model database. The original proband tooth models can then be constructed from these.

Subsequently, morphological difference values of the determined matching proband tooth models to the corresponding tooth models of the shapes linkage group are computed. Computation of a morphological difference value can be done simply and reliably using the sum of squares of difference values between vertices of two tooth models that are to be compared, once both tooth models have been aligned as optimally as possible through translation and rotation. The morphological difference value determined in this manner is referred to in the following as the correspondence-deviation value. Five match-deviation values are subsequently determined for each of the six tooth models of the shapes linkage group in the above example. The shapes optimization partial value for the linking of the tooth model shapes is then given by the sum of squares of these match-deviation values.

The optimization partial values described above can be computed in a fully automated manner, i.e. without requiring any user interaction. In the above embodiment, the corresponding quality partial values determine, for example by falling below a defined threshold, whether the user should be prompted to label structures in the scan data to also be used in the individualization of tooth models in a subsequent process cycle. In other words, in a subsequent process cycle, besides the previously used optimization partial values, optimization partial values on the basis of user interaction are also considered. For example, if the quality value of a tooth model for the adjustment to tooth structure or residual tooth structure lies below a threshold, the user is prompted to label unprepared tooth surfaces or residual tooth structure. In the above embodiment, since the preparation types are known, the user is prompted, for example, to label unprepared tooth structure for preparation types that implicate the presence of unprepared tooth structure. These might be, for example, the "tooth", "inlay", "onlay", etc. preparation types.

An important optimization partial value, on the basis of user interaction, describes the adjustment of a tooth model to the corresponding labeled unprepared tooth surfaces in the scan data. Preferably, for each marked scan element, the minimum distance to the corresponding tooth model surface is determined and a mean distance is computed using these values. The square of this distance value can be used as optimization partial value. Preferably, unprepared tooth surfaces that belong to the first and/or last tooth model in the model group are labeled first in the scan data. In a completely analogous manner, these calculations can be used for the determination of optimization partial values that describe the contact points to the opposing dentition and/or to adjacent teeth.

It is advantageous to work with prefixed distance values when adjusting a tooth model to the corresponding labeled residual tooth structure in the scan data. At least one method of computation for prefixed distance values has already been described above. A negative prefix indicates that a labeled scan element lies within the tooth model, and a positive prefix indicates that a marked scan element lies outside. These prefixed distance values are determined for all labeled scan elements, and the square of the maximum of these distance values is used as optimization partial value.

Computation of an optimization partial value for the adjustment of a tooth model to a segmentation line labeled by the user in the scan data—for instance by a single mouse-click—can also be performed by using distance values. To this end, concave surface structures that form a transition from the teeth to the gums are usually labeled as parts of segmentation lines. To calculate the corresponding optimization partial value, the minimum distance to the segmentation line of the corresponding tooth model is preferably determined for each labeled scan element. The square of the mean distance value of all distances determined in this way is then used for the optimization partial value. The optimization partial value for the adjustment of a tooth model to a labeled preparation line is carried out in a completely analogous manner, whereby, in contrast to segmentation lines, preparation lines are characterized by convex surface structures.

A further optimization partial value describes the adjustment of a tooth model to a labeled anatomical landmark in the scan data. In a preferred embodiment, to compute such an optimization partial value, distances are computed between the labeled anatomical landmarks in the scan data to the corresponding landmarks of the tooth model. The optimization partial value is then given by the sum of the squares of these distance values. In the same way, an optimization partial value can also be computed for the adjustment of a tooth model to artificial oral structures. For example, a tooth model can also comprise an implant model. This implant model preferably comprises landmarks that can be labeled in the scan data. The resulting optimization partial value is given by the distances from corresponding implant landmarks.

Figure 5:
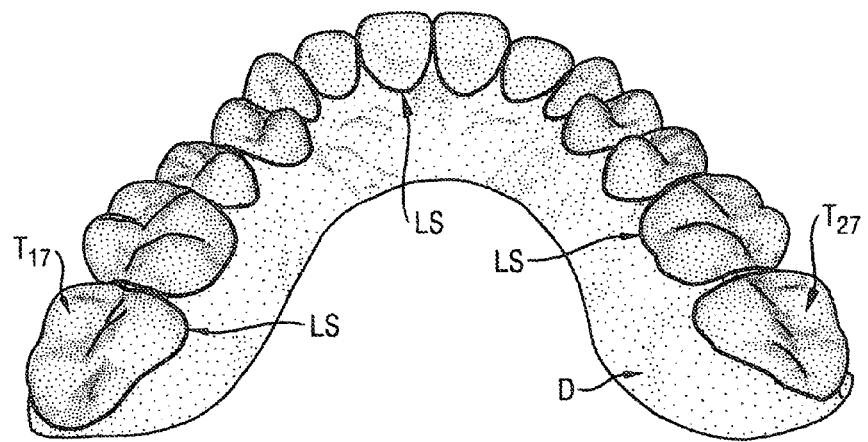
FIG. 5 shows a perspective view of scan data D of an upper jaw with segmented teeth T17 to T27 and determined segmentation lines LS.
Figure 7:
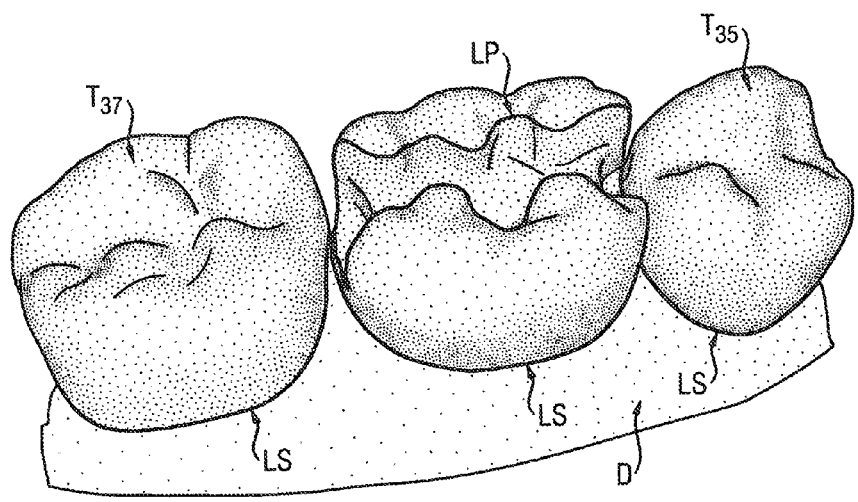
FIG. 7 shows a perspective view of scan data D of a partial upper jaw with segmented teeth T35 to T37 and determined segmentation lines LS and a determined preparation line LP.

To increase the precision of the results of the method, a precision adjustment of the individualized tooth models with their individualized boundary lines LS, LP can be carried out relative to each other and/or to the scan data D prior to the subsequent geometrical analysis of the scan data D. It is advantageous to perform deformation transformations on the individualized tooth models, to perform a precision adjustment of the tooth models relative to each other and also relative to the teeth, residual tooth structure, opposing dentition, bite registrations, contact points etc., using displacement values that are as small as possible and that do not generate any edges or folds. These adjustments can be carried out analogously to the individualization of tooth models, whereby the parameters of the deformation transformation are used here as optimization parameters. The manner of computation of the optimization value to be minimized from optimization partial values can be adopted unchanged. A possible geometrical transformation for the precision adjustment of a tooth model is described in the thesis "Individualization of digital anatomical models using computer tomography" (M. Tank, 2002, Heidelberg University Forensic Medicine Institute). FIG. 5 of this document shows segmentation lines LS for a jaw scan of teeth 17 through 27, precisely adjusted in this manner, while FIG. 7 shows precisely adjusted boundary lines LS, LP for an inlay preparation.

The computation of individualized tooth models takes place within an individualizing unit 15, realized in this case in the form of a software module on the processor 13 of the computer 10 (cf. FIG. 19). The individualizing unit 15 has access to the model database DB in the memory 12 of the computer 10, in order to load corresponding tooth models and their geometric transformations for selected tooth types. Furthermore, the individualizing unit requires access to further information in the model database, for example to the proband shape parameters, in order to compute shape optimization partial values for shapes linkage groups.

Figure 6:
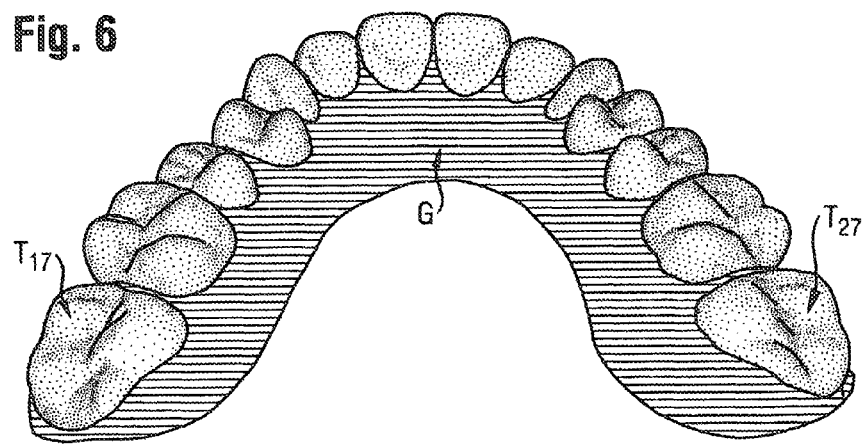
FIG. 6 shows a perspective view of scan data D of an upper jaw with segmented teeth T17 to T27 and segmented gum G.
Figure 8:
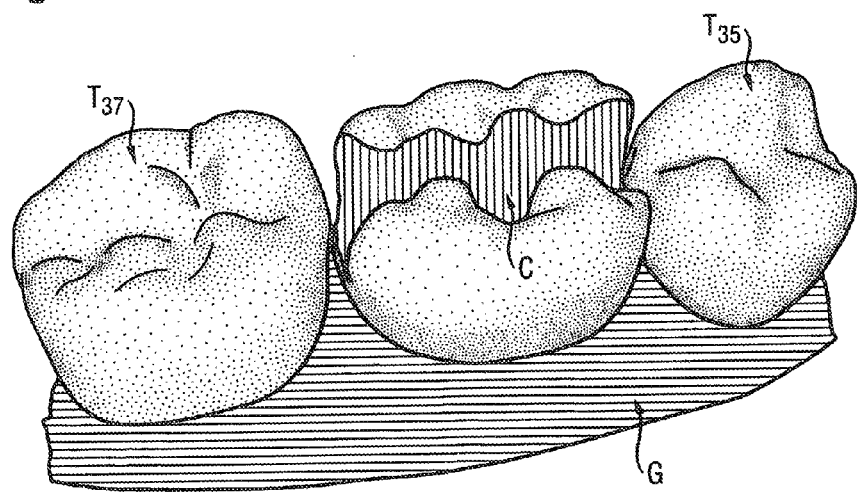
FIG. 8 shows a perspective view of scan data D of a partial upper jaw with segmented teeth T35 to T37 and a segmented cavity C and segmented gum G.

The scan data are then segmented on the basis of the individualized tooth models with their individualized boundary lines. FIG. 6 shows an example of a segmented jaw bone scan, in which the segmented gum G is depicted by the hatched area. FIG. 8 shows segmented scan data D with an inlay preparation, in which a cavity C for the inlay preparation is also shown by a hatched area, in addition to the gum G. During segmentation, each scan element (for example vertices in the case of optical scans, voxels in the case of radiological scans) is assigned a tooth number, for example, or a number that indicates extradental structures. These numbers can be color-coded and, with of a suitable coloration of the scan data, allow a quick visual check by the user of the segmentation results. The assigning of tooth numbers to scan elements can be done using various methods. A simple approach first determines, for a scan element, the minimum distances to each single individualized tooth model, wherein a negative prefix is used for a distance when the scan element lies within the individualized tooth model. Subsequently, the tooth number of the individualized tooth model with the smallest distance is determined and assigned to the scan element. If this distance is greater than a positive threshold value, a predefined number is used for the scan element to identify extradental structures.

In this method, cavities are distinguished in that the minimum distance of a scan element to a corresponding tooth model lies below a negative threshold value. Corresponding labeling of cavities C may also be assigned to the tooth numbers of the scan elements. A further differentiation of the results can be carried out in that only parts of the individualized tooth models are subsequently considered during the computation. In this way, further labels, describing single partial models or surface regions such as roots or cusps can be added to the scan elements.

Figure 2:
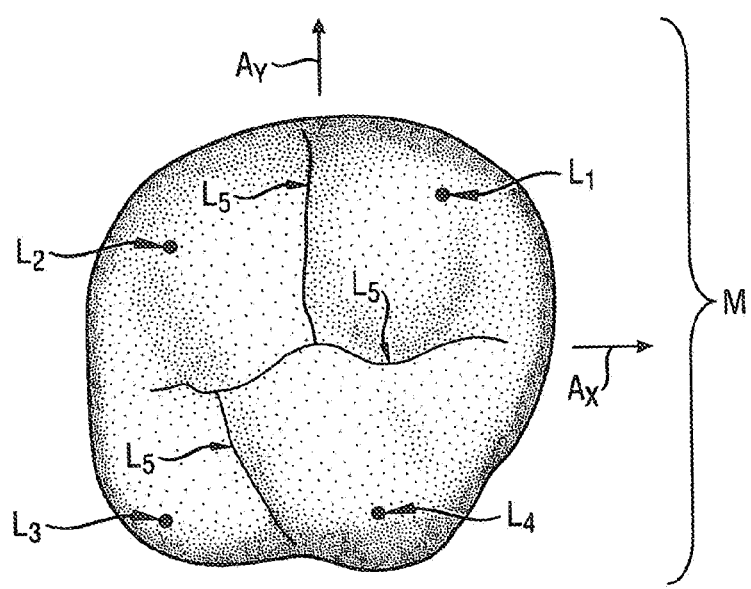
FIG. 2 shows a perspective view of a tooth model M with anatomical landmarks L1, L2, L3, L4, L5 and tooth axes AX, AY.
Figure 9:
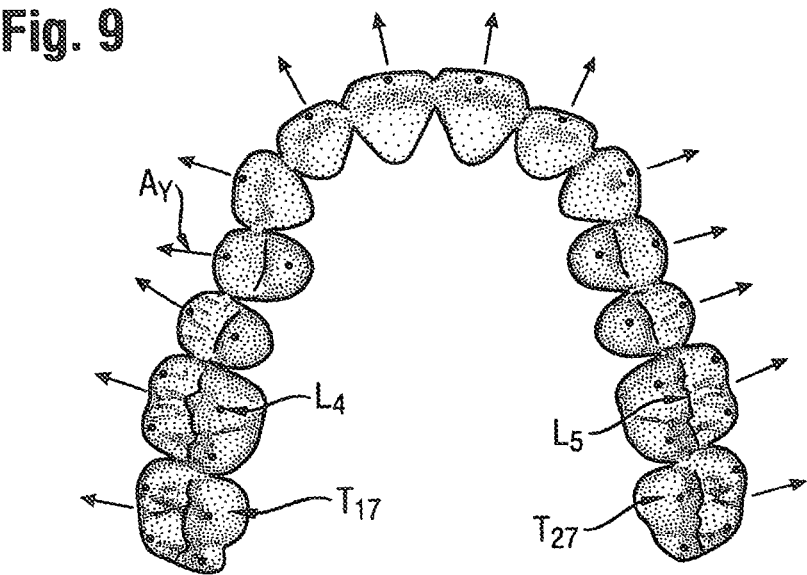
FIG. 9 shows a perspective view of segmented teeth T17 to T27 according to FIG. 5 and determined tooth axes AY and determined anatomical landmarks L4, L5.
Figure 10:
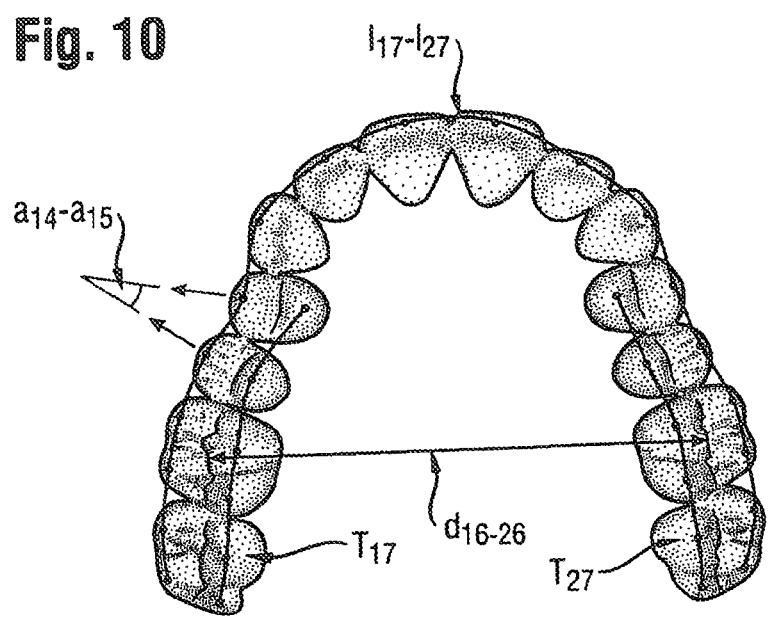
FIG. 10 shows a perspective view of segmented teeth T17 to T27 according to FIG. 5 and a determined angle a14-a15 between two tooth axes, a determined distance d16-26 between two anatomical landmarks and a determined length l17-l27 of a line connecting anatomical landmarks.

The determination of segmentation lines LS, preparation lines LP, anatomical landmarks L1, L2, L3, L4, L5, tooth axes AX, AY, directional terms and other characteristic geometric structures in the scan data D is done by transferring the corresponding structures, labeled on the tooth models M (cf. FIG. 2), to the scan data D. FIG. 9 shows a perspective view of segmented teeth T17 to T27, and tooth axes AY and anatomical landmarks L4, L5 determined in this manner. Furthermore, the scan data D can be measured on the basis of these individualized structures. FIG. 10 shows a perspective view of segmented teeth T17 to T27 and a determined angle $a_{14}$-$a_{15}$ between two tooth axes, a determined distance $d_{16-26}$ between two anatomical landmarks, and a determined length $l_{17}$-$l_{27}$ of a line connecting anatomical landmarks.

This further geometrical analysis of the scan data, on the basis of the individualized tooth models, takes place within an analysis unit 16, which in this case is also in the form of a software module on the processor 13 of the computer 10, following the individualization unit 15.

The tooth restorations R and/or preparation types (inlay, crown, bridge, etc.) of the scanned teeth can also be determined on the basis of the individualized tooth models and scan data (cf. FIG. 4). These preparation types, determined algorithmically, allow a checking of the method results in the previous example, by comparing them with the preparation types specified by the user. The determination of tooth restorations R and preparation types can also take place in the analysis unit 16.

The tooth restorations R can be determined from the individualized tooth models M and scan data D using standard methods known to the skilled person. Basically, the preparation lines of the scan data D are joined in a suitable manner to the individualized tooth model M, continuously and smoothly, and the cavities are subsequently added as lower boundaries. The result is three-dimensional models of milling objects for the tooth restorations R that can be machined. FIG. 3 shows exemplary scan data D with optimal tooth models M for typical inlay, crown and bridge preparations. FIG. 4 shows the corresponding tooth restorations R.

The determining of preparation lines is preferably performed on the basis of the typical characteristic geometric shapes of the determined virtual tooth restorations and the corresponding boundary lines. For example, in a crown preparation, the segmentation lines and preparation lines lie relatively close together everywhere, and are located roughly at gum level, and the occlusion area of the corresponding individualized tooth model is completely prepared. In a typical veneer preparation, on the other hand, the preparation line lies orally at gum level and lingually just behind the prepared incisor edge, i.e. significantly more occlusal. Usually, the preparation line extends mesially and distally close to the adjacent teeth, after all it is a completely bonded veneer in the incisor area. The corresponding individualized tooth model exhibits a complete preparation of the incisor edge and the oral parts above the gum. The greatest variation of the preparation lines occurs in inlay preparations. Because of the residual tooth structure, from an occlusal point of view at least part of the preparation line is found in the region of the tooth center, and this part also exhibits a relevant distance to the segmentation line. in contrast to the other two preparation types, the occlusal region of the individualized tooth model is not completely prepared, instead at least one cusp is still present.

The qualitative descriptions to determine the preparation type can be expressed in mathematical calculations. The occlusal regions of the posterior teeth and the incisor edges of the incisors can be labeled on the tooth models. With the individualized preparation lines, inactive model areas are obtained that correspond to prepared regions of the scanned teeth. The percentage of the prepared occlusal surface or the incisor edge of an individualized tooth model can be used in a case-by-case analysis.

Figure 15:
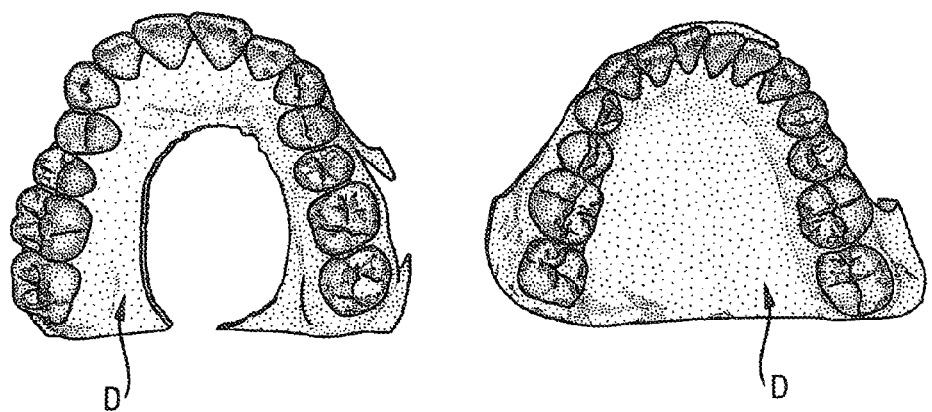
FIG. 15 shows a perspective view of scan data D of a jaw, used in the building of a model database, wherein the left-hand side shows the maxilla scan, and the right-hand side shows the mandible scan.

One embodiment of a method according to the invention of building at least parts of a model database is characterized by carrying out an analysis of a representative set of scan data D of defect-free upper and lower jaws. The use of plaster jaw impressions is suggested, since these are economical and can be precisely scanned optically. FIG. 15 shows optical scan data D generated in this manner. It is emphasized here again that the database build can also be carried out by an analysis of radiological data or even by an analysis of a combination of both types of data.

For the analysis of shape variations of the individual teeth, it is advantageous to segment the scan data D in a first step of database building, wherein this segmentation can preferably be carried out interactively with the aid of a graphical user interface. The result of the segmentation of jaw scan data D is a set of tooth scan data sets for each tooth type (in this case: tooth number), which can be used to build at least part of a model database.

Figure 16:
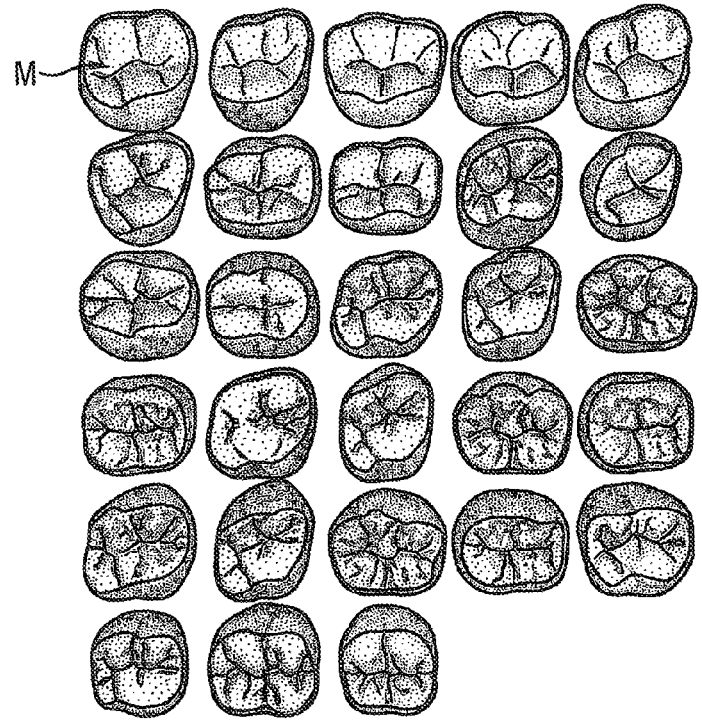
FIG. 16 shows a perspective view of tooth models M of a tooth type, constructed by adjustment to scan data originating from the segmentation of jaw scans of a tooth type.

The construction of tooth models M of a tooth type takes place in a second step of the database building. Depending on the desired spatial resolution, a tooth model M is constructed for each tooth scan data set. To this end, a tooth model M can first be constructed, which consists of a triangulated surface in the form of a cuboid, with the dimensions of the tooth scan data set, whereby the triangulation delivers a desired resolution by successive subdivision of the side faces of the cuboid. Subsequently, an adjustment of the initially constructed tooth model M to the tooth scan data set takes place, for example by minimizing the sum of the squares of the distance values of the tooth model vertices to the tooth surface in the that tooth scan data set. FIG. 16 shows tooth models M of a tooth type that have been constructed in this manner.

Figure 17:
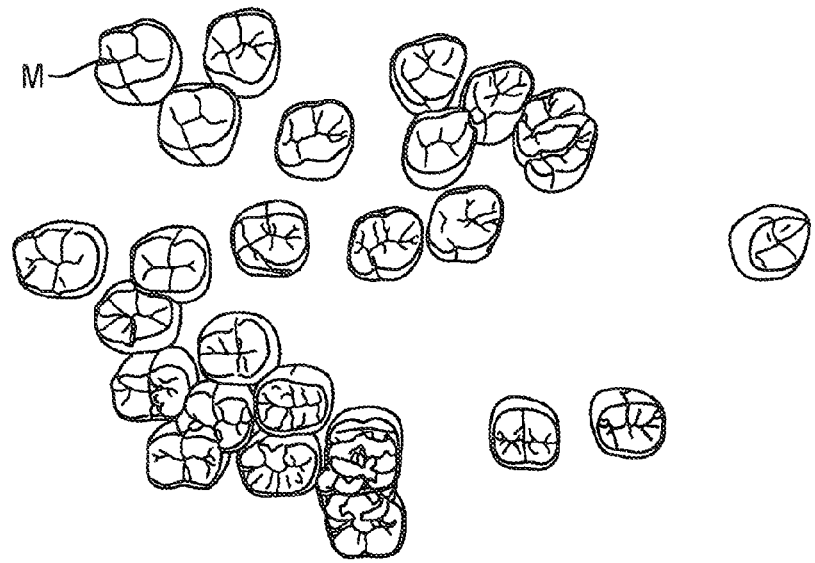
FIG. 17 shows a perspective view of an array of tooth models M of a tooth type, defined by mutual morphological difference values, whereby morphologically similar tooth models M are separated by a shorter spatial distance in the array.

Subsequently, in a third step of database building, an analysis of the morphological deviations among the tooth models M of a tooth type is carried out by computing a morphological difference value for each possible pair of tooth models M. To this end, both tooth models M of a pair are preferably aligned by an optimal translation and rotation such that the sum of the squares of the difference values of the tooth model vertices is minimized. For the distance value of a tooth model vertex of the first tooth model M of the pair, the minimum distance of the vertex to the surface of the second tooth model M of the pair can be used. The mean distance value of the tooth model vertices remaining after the adjustment can be used as the morphological deviation value for the tooth model pair. A visualization of the results is preferably done by a two-dimensional array of the tooth models M as shown in FIG. 17. This array is defined in that the distances of the tooth models M to each other, up to a common scaling factor, correspond as far as possible to the corresponding morphological difference values of the tooth models M. In a fourth database building step, a mean tooth model MM is determined for each tooth type, whereby preferably that tooth model M is selected, whose sum of squares of morphological difference values is least for all tooth models M of that tooth type. That tooth model M will be regarded subsequently as the mean tooth model MM of that tooth type.

In a fifth database building step, a sorting of the tooth models M of a tooth type takes place on the basis of the computed morphological difference values. To set up such a sorting, the sorting can commence with the mean tooth model MM and can iteratively add further tooth model M of the same tooth type. The most recently added tooth model M is referred to as the current tooth model M. The sorting criterion can be defined as always adding that tooth model M whose sum of squares of morphological difference values is greatest compared to the already sorted tooth models M.

Figure 18:
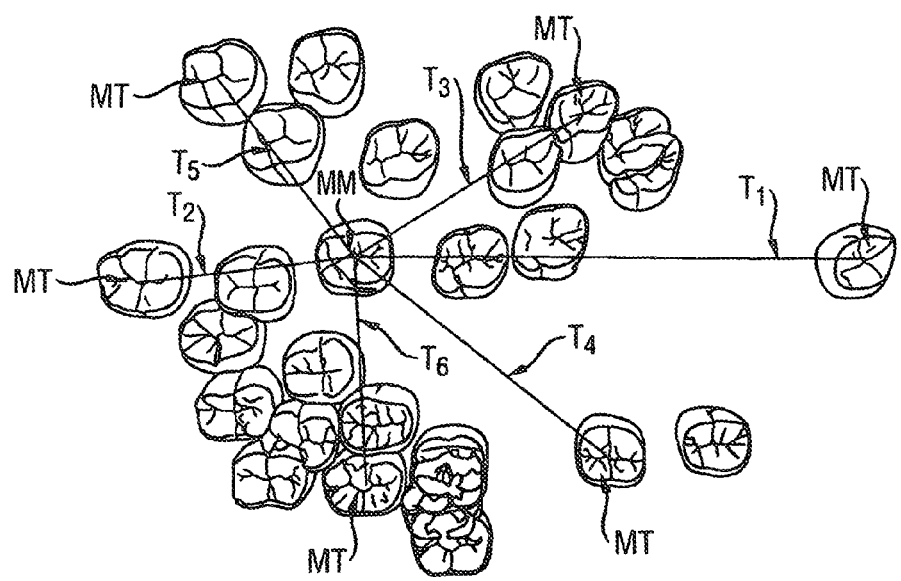
FIG. 18 shows a perspective view of a possible sorting of seven tooth models M, comprising a mean tooth model MM and six target tooth models MT, of a model database with six partial transformations T1, T2, T3, T4, T5, T6.

In a final sixth database building step, another parameterized geometrical transformation is added to the mean tooth model MM, preferably defined in that the shape of the mean tooth model MM can be continually transformed to at least one target tooth model MT appearing further on in the sorting. This geometrical transformation preferably comprises geometrical partial transformations, in which the transformation is preferably a linear combination of the partial transformations. Each separate transformation transforms the mean tooth model MM into a target tooth model MT. FIG. 18 shows an example for a sorting of seven tooth model M, consisting of a mean tooth model MM and six target tooth models MT, with six corresponding partial transformations T1, T2, T3, T4. T5, T6. These six target tooth models MT are the first tooth models that come after the mean tooth model MM in the fifth step of sorting during building of a database, and are therefore the tooth models with the greatest morphological differences from the mean tooth model MM and the previously sorted tooth models (in this case the previously sorted other target tooth models MT). The number of target tooth models MT can result from specifying a threshold value for morphological difference values. To this end, preferably the number of target tooth models MT is increased and the corresponding geometrical transformation is constructed each time until all tooth models M of the tooth type result from application of the constructed geometrical transformation up to the specified threshold value.

The first step in the construction of the geometrical transformation preferably comprises a fragmentation of the bounding box of the mean tooth model MM in axis-parallel cells of the same size. Translation vectors of the cell nodes then define a tri-linear transformation of the tooth model vertices. This approach is explained in detail in the thesis "Individualization of digital anatomical models using computer tomography" (M. Tank, 2002, Heidelberg University Forensic Medicine Institute), and is also referred to therein as a cell method. The result is a transformation, in which the transformation parameters are arranged hierarchically according to their weight. The transformation parameters for a morphing between the mean tooth model MM and a target tooth model MT result from the requirement that the sum of the squares of the distance values of the transformed mean tooth model MM must be minimal to the target tooth model MT, and that local surface properties should be maintained as far as possible. A linear combination of the transformation parameters obtained in this way results in morphologically reasonable variations of the mean tooth model MM. The shape parameter of the mean tooth model MM then preferably comprises the linear factors defined in this way.

In addition to the building of at least parts of a model database on the basis of scan data of natural oral structures, scan data of artificial oral structures can also be used. The building method for such a model database corresponds to the building method for natural oral structures, and is carried out in a completely analogous manner. The first step of database building can be dispensed with. The first step of database building, i.e. the segmentation of the scan data, is usually not necessary, since the artificial oral structures (for example artificial teeth such as tooth prostheses or unmachined tooth prostheses) are physically separate and can be scanned separately.

It shall be emphasized here again that the system architectures and processes shown in the diagrams are only exemplary embodiments that can be modified as required by the skilled person. In particular, the control unit, insofar as it is equipped with a suitable console, can also comprise all relevant components of the computer in order to carry out the processing of the measurement data using the method according to the invention. In this case, it follows that the control unit itself acts as the analysis system according to the invention, and a further or separate computer is not necessary. Furthermore, it is also not necessary that the various components of an analysis system according to the invention be realized on one processor or in one computer, but can be distributed over several processors or networked computers. For the sake of completeness, it shall be pointed out that the use of the indefinite article "a" or "an" does not exclude a plurality. Equally, the terms "apparatus", "facility", "unit", "module" etc. do not exclude that these may comprises several components, which also may be distributed in any manner.

Furthermore, it is possible to upgrade existing analysis systems that implement known post-processing procedures with a process control unit according to the invention, so that such systems can also be used for the method according to the invention as described above. In many cases, it may suffice to update the control software with suitable control software modules.

The invention claimed is:

1. Method for the geometrical analysis of scan data (D) from oral structures, comprising the steps of
    selecting a number of parameterized tooth models (M) of desired tooth types according to the scan data (D) to be analyzed, whereby the parameterization is performed on the basis of model parameters comprising position parameters, shape parameters and line parameters, and whereby each tooth model (M) comprises at least one boundary line (LS, LP) whose path is defined by line parameters and which divides a tooth model (M) in at least one active adjustment area (AA) and at least one inactive adjustment area (AI),
    adjusting the tooth models (M) and their boundary lines (LS, LP) to the scan data (D) for individualization, whereby the individualization is performed by variation of model parameters, and whereby the active adjustment areas (AA) of the tooth models (M) are weighted more than the inactive adjustment areas (AI), wherein after individualization of the tooth models (M) and prior to a further geometric analysis of the scan data, a fine adjustment is carried out of the individualized tooth models (M) with their individualized boundary lines (LS, LP) with respect to each other and to the scan data; stabilizing of the individualization by simultaneously adjusting the tooth models at a global level and adjusting the boundary lines at a local level,
    segmenting the scan data (D) on the basis of at least one of: of the individualized tooth models (M) and their individualized boundary lines (LS, LP); and determining at least one boundary line (LS, LP) in the scan data (D) on the basis of the individualized models (M) and their individualized boundary lines (LS, LP).

2. Method according to claim 1, further including at least one of: the boundary lines (LS, LP) lie on the surface of the tooth models (M); the boundary lines (LS, LP) comprise a parameterized separation to the surfaces of the tooth models (M); and at least one of: the line parameters are chosen such that the boundary lines (LS, LP) do not intersect; and the line parameters are chosen such that the boundary lines (LS, LP) maintain a minimum separation from each other.

3. Method according to claim 1, wherein the boundary lines (LS, LP) of a tooth model (M) comprise at least one of: at least one segmentation line (LS); and at least one preparation line (LP); and wherein
    a segmentation lines target structure, consisting of portions of scan data (D) and comprising at least one concave surface structure, is preferably determined for the individualization of the segmentation lines (LS);
    a preparation lines target structure, consisting of portions of scan data (D) and comprising at least one convex surface structure, is preferably determined for the individualization of the preparation lines (LP).

4. Method according to claim 1, wherein the adjustment areas (AA, AI) lie on the tooth model surfaces and that, in the case of optical scan data (D), the active adjustment areas (AA) are adjusted to unprepared tooth surfaces in the scan data (D) and, in the case of radiological scan data (D), to unprepared tooth surfaces that lie beyond the gum or beyond the jawbone or comprise tooth enamel.

5. Method according to claim 1, wherein a quality value is computed for the individualization of tooth models (M), which quality value comprises individual quality partial values, which describe compliance with individualization criteria and which determine whether the user will be required to label structures in the scan data, which labels are used in the individualization of tooth models (M) in a repeated process cycle.

6. Method according to claim 1, wherein, for a tooth model (M), the weighting of the adjustment areas (AA, AI) is carried out on the basis of the quality partial values for the individualization of the boundary lines (LS, LP), whereby, with increasing quality partial values for the individualization of the boundary lines (LS, LP), the active adjustment areas (AA, AI) are weighted more in the adjustment to the scan data (D).

7. Method according to claim 1, further including at least one of: anatomic landmarks (L1, L2, L3, L4, L5); tooth axes (AX, AY); directional terms; surface regions; further characteristic geometric structures are labeled on the tooth models (M) and transferred to the scan data (D) after individualization; and a geometric measurement (d16-26, a14-15, l17-27) of the scan data (D) is performed on the basis of these individualized structures.

8. Method according to claim 1, wherein virtual tooth restorations (R) of prepared teeth are determined from the individualized tooth models (M) and scan data (D) and that the preparation types of the teeth associated with the tooth models (M) are determined from at least one of: the characteristic geometric shapes of the determined virtual tooth restorations (R); and the individualized boundary lines (LS, LP) belonging to the individualized tooth models (M); and that at least one of optional verbal and symbolic descriptors for these determined preparation types are displayed using at least one of a dental notation system; a reduced dental notation system; and graphically using the scan data (D).

9. Method according to claim 1, wherein the individualization of tooth models (M) is performed by solving an optimization problem, in which an optimization value results from a number of optimization partial values, whereby at least certain optimization partial values are particularly preferably chosen to satisfy at least one of the following individualization criteria:
    at least one of the adjustment of tooth models (M) to teeth and remaining tooth structure,
    the adjustment of tooth models (M) to opposing dentition,
    the adjustment of tooth models (M) to bite registrations,
    the adjustment of tooth models (M) to artificial oral structures,
    the adjustment of boundary lines (LS, LP) of the tooth models (M) to structures in the scan data (D) with corresponding surface curvatures,
    the mechanical stability of virtual tooth restorations (R) belonging to the tooth models (M),
    the aesthetic effect of virtual tooth restorations (R) belonging to the tooth models (M),
    the contacts of tooth models (M),
    the spatial relations of the positions of tooth models (M),
    the spatial relations of the shapes of tooth models (M).

10. Method according to claim 9, wherein structures are labeled in the scan data (D) and optimization partial values are computed that describe deviations of the labeled structures to corresponding structures of the tooth models (M), whereby preferably at least one label describes one of the following structures:
    unprepared surfaces of teeth,
    remaining tooth structure of teeth,
    segmentation lines of teeth, preparation lines of teeth,
anatomic landmarks of teeth,
artificial oral structures,
contact points to neighboring teeth,
contact points to opposing dentition.

11. Method of generating a model database (DB) comprising a number of parameterized tooth models (M) for each of a number of different tooth types, for use in the method according to claim 1, whereby parameterization is performed on the basis of model parameters, which comprise at least one of parameters, and shape parameters and line parameters, and whereby each tooth model (M) comprises at least one parameterized boundary line (LS, LP) whose path is described by line parameters and which divides a tooth model (M) in at least one active adjustment area (AA) and at least one inactive adjustment area (AI).

12. Method according to claim 11, wherein at least parts of the model database (DB) are built up by the analysis of at least one of a set of optical scan data (D) of oral structures and radiological scan data (D) of oral structures, for which, for a desired tooth type
the scan data (D) are optionally segmented in order to obtain scan data (D) of the desired tooth type,
tooth models (M) of the model database (DB) are constructed by an adjustment to the scan data (D) of the desired tooth type,
an analysis of morphological deviations is performed among the tooth models (M), in which a morphological difference value is computed for each possible pair of tooth models (M),
a mean tooth model (MM) is chosen on the basis of morphological difference values,
a sorting of tooth models (M) is generated by commencing with a mean tooth model (MM) and adding remaining tooth models (M) to the sort on the basis of morphological difference values to the already sorted tooth models (M), whereby tooth models (M) with significantly different morphology are at the beginning of the sort,
a parameterized geometrical transformation is added to the mean tooth model (MM), defined in that the shape of the mean tooth model (MM) can be smoothly converted to at least one subsequent tooth model (MT) in the sort.

13. A computer program product, directly loadable in a non-transitory computer-readable medium of a computer, comprising program code means for carrying out all steps of a method according to claim 1 when said computer program product is run on the computer.

14. A computer program product, directly loadable in a non-transitory computer-readable medium of a computer, comprising program code means for carrying out all steps of a method according to claim 11 when said computer program product is run on the computer.

15. A computer program product, directly loadable in a non-transitory computer-readable medium of a computer, comprising program code means for carrying out all steps of a method according to claim 12 when said computer program product is run on the computer.

16. Analysis system (5) for the geometrical analysis of scan data (D) from oral structures, comprising
an interface (11) for receiving scan data (D) measured by a measurement means,
a memory means (12) comprising parameterized tooth models (M), whereby the parameterization is carried out on the basis of model parameters comprising at least one of position parameters, and shape parameters and line parameters, and whereby each tooth model (M) comprises at least one parameterized boundary line (LS, LP), whose path is described by line parameters and which divides a tooth model (M) in at least one active adjustment area (AA) and at least one inactive adjustment area (AI),
a selection unit (14) for defining the range of the tooth models (M) to be used by the procedure,
an Individualization unit (15) in which the tooth models (M) with their boundary lines (LS, LP) are adjusted to the scan data (D) for individualization, whereby this Individualization is performed by variation of model parameters and whereby the active adjustment areas (AA) of the tooth models (M) are weighted more than the inactive adjustment areas (AI), wherein after individualization of the tooth models (M) and prior to a further geometric analysis of the scan data, a fine adjustment is carried out of the individualized tooth models (M) with their individualized boundary lines (LS, LP) with respect to each other and to the scan data; stabilizing of the individualization by simultaneously adjusting the tooth models at a global level and adjusting the boundary lines at a local level,
and an analysis unit (16) in which the scan data (D) are segmented on the basis of at least one of: the individualized tooth models (M) with their individualized boundary lines (LS, LP); and at least one boundary line (LS, LP) is determined in the scan data (D) on the basis of the individualized tooth models (M) and their individualized boundary lines (LS, LP).

* * * * *